United States Patent
Main et al.

(10) Patent No.: US 12,310,742 B2
(45) Date of Patent: May 27, 2025

(54) INTELLIGENT WEIGHT SUPPORT SYSTEM

(71) Applicant: XSENSOR Technology Corporation, Calgary (CA)

(72) Inventors: Ian Main, Calgary (CA); Mohammad Najafi, Calgary (CA); Mitchell Robert Knight, Calgary (CA); Adele Syt Fu Chui, Calgary (CA); Dylan Heckbert, Calgary (CA); Murray Vince, Seattle, WA (US)

(73) Assignee: Xsensor Technology Corporation, Calgary (CA)

( * ) Notice: Subject to any disclaimer, the term of this patent is extended or adjusted under 35 U.S.C. 154(b) by 307 days.

(21) Appl. No.: 17/019,090

(22) Filed: Sep. 11, 2020

(65) Prior Publication Data
US 2022/0079514 A1 Mar. 17, 2022

(51) Int. Cl.
*A61B 5/00* (2006.01)
*A47C 21/00* (2006.01)
(Continued)

(52) U.S. Cl.
CPC ............ *A61B 5/4812* (2013.01); *A47C 21/00* (2013.01); *A61B 5/0205* (2013.01);
(Continued)

(58) Field of Classification Search
None
See application file for complete search history.

(56) References Cited

U.S. PATENT DOCUMENTS

| | | | |
|---|---|---|---|
| 2,378,039 | A | 6/1945 | Schenker |
| 2,804,129 | A | 8/1957 | Propst |

(Continued)

FOREIGN PATENT DOCUMENTS

| | | |
|---|---|---|
| AU | 48619/93 | 5/1994 |
| AU | 649391 B3 | 5/1994 |

(Continued)

OTHER PUBLICATIONS

PCT International Search Report and Written Opinion, PCT Application No. PCT/IB2021/000598, Feb. 18, 2022, 14 pages.

(Continued)

*Primary Examiner* — Aurelie H Tu
(74) *Attorney, Agent, or Firm* — Fenwick & West LLP

(57) ABSTRACT

Embodiments may relate to an air-permeable weight support system, which may include a microclimate fabric layer and an air-permeable capacitive sensor layer below the microclimate fabric layer. The air-permeable capacitive sensor layer may include two air-permeable substrates, each carrying a plurality of electrically conductive pathways that are impermeable to air. The two air-permeable substrates may securely position the electrically conductive pathways to define a sensor grid and position the electrically conductive pathways that are impermeable to air to be spaced apart to define a plurality of air pathways for the air-permeable capacitive sensor layer. The sensor data may be used to determine a sleep state of the person using the weight support system. A computer may identify the poses of the person based on the pressure sensor data. A machine learning model may rely on the poses, the heart rates, the respiration rates to determine the sleep state.

9 Claims, 19 Drawing Sheets

(51) Int. Cl.
　　　*A61B 5/0205*　　(2006.01)
　　　*A61B 5/11*　　　(2006.01)
　　　*G06N 20/00*　　 (2019.01)
　　　*A47G 9/02*　　　(2006.01)
　　　*A47G 9/10*　　　(2006.01)
　　　*A61B 5/024*　　 (2006.01)
　　　*A61B 5/08*　　　(2006.01)
　　　*A61G 7/05*　　　(2006.01)

(52) U.S. Cl.
　　　CPC ........ *A61B 5/02055* (2013.01); *A61B 5/1114* (2013.01); *A61B 5/6892* (2013.01); *A61B 5/7264* (2013.01); *G06N 20/00* (2019.01); *A47G 9/0246* (2013.01); *A47G 2009/1018* (2013.01); *A47G 9/1045* (2013.01); *A61B 5/0022* (2013.01); *A61B 5/024* (2013.01); *A61B 5/0816* (2013.01); *A61B 5/0823* (2013.01); *A61B 5/1117* (2013.01); *A61B 5/4094* (2013.01); *A61B 5/7225* (2013.01); *A61B 5/725* (2013.01); *A61B 2562/0214* (2013.01); *A61B 2562/0219* (2013.01); *A61B 2562/0247* (2013.01); *A61B 2562/0261* (2013.01); *A61B 2562/0271* (2013.01); *A61G 7/0527* (2016.11)

(56) References Cited

U.S. PATENT DOCUMENTS

| | | | |
|---|---|---|---|
| 2,976,725 | A | 3/1961 | Byer |
| 3,100,992 | A | 8/1963 | Davis |
| 3,195,347 | A | 7/1965 | Janapol |
| 3,334,517 | A | 8/1967 | Janapol |
| 3,413,849 | A | 12/1968 | Janapol |
| 3,565,195 | A | 2/1971 | Miller et al. |
| 3,826,926 | A | 7/1974 | White et al. |
| 3,875,481 | A | 4/1975 | Miller et al. |
| 4,005,438 | A | 1/1977 | Meltzer et al. |
| 4,134,063 | A | 1/1979 | Nicol et al. |
| 4,266,263 | A | 5/1981 | Haberl et al. |
| 4,370,697 | A | 1/1983 | Haberl et al. |
| 4,554,930 | A | 11/1985 | Kress |
| 4,584,625 | A | 4/1986 | Kellogg |
| 4,662,012 | A | 5/1987 | Torbet |
| 4,827,763 | A | 5/1989 | Bourland et al. |
| 4,847,933 | A * | 7/1989 | Bedford ............... A61G 5/1091 |
| | | | 5/652.2 |
| 4,986,136 | A | 1/1991 | Brunner et al. |
| 5,010,772 | A | 4/1991 | Bourland et al. |
| 5,148,706 | A | 9/1992 | Masuda et al. |
| 5,231,717 | A | 8/1993 | Scott et al. |
| 5,306,912 | A | 4/1994 | Sibbald et al. |
| 5,401,922 | A | 3/1995 | Asta |
| 5,447,076 | A | 9/1995 | Ziegler |
| 5,487,196 | A | 1/1996 | Wilkinson et al. |
| 5,514,832 | A | 5/1996 | Dusablon et al. |
| 5,653,939 | A | 8/1997 | Hollis et al. |
| 5,693,886 | A | 12/1997 | Seimiya et al. |
| 5,745,940 | A | 5/1998 | Roberts et al. |
| 5,815,865 | A | 10/1998 | Washburn et al. |
| 5,848,450 | A | 12/1998 | Oexman et al. |
| 5,963,997 | A | 10/1999 | Hagopian |
| 5,970,789 | A | 10/1999 | Meyer et al. |
| 5,993,400 | A | 11/1999 | Rincoe et al. |
| 6,192,538 | B1 | 2/2001 | Fogel |
| 6,280,392 | B1 | 8/2001 | Yoshimi et al. |
| 6,585,328 | B1 | 7/2003 | Oexman et al. |
| 6,826,968 | B2 | 12/2004 | Manaresi et al. |
| 7,067,979 | B2 | 6/2006 | Sakamoto |
| 7,107,642 | B2 | 9/2006 | Wong et al. |
| 7,378,975 | B1 | 5/2008 | Smith et al. |
| 7,467,058 | B2 | 12/2008 | Boyd |
| 7,580,030 | B2 | 8/2009 | Marten |
| 7,609,178 | B2 | 10/2009 | Son et al. |
| 7,638,350 | B2 | 12/2009 | Deconde et al. |
| 7,937,239 | B2 | 5/2011 | Boyd |
| 8,011,041 | B2 | 9/2011 | Hann |
| 8,121,800 | B2 | 2/2012 | Altman et al. |
| 8,272,276 | B2 | 9/2012 | Gorjanc et al. |
| 8,458,042 | B1 | 6/2013 | Roberts et al. |
| 8,463,006 | B2 | 6/2013 | Prokoski |
| 8,544,336 | B2 | 10/2013 | Main et al. |
| 8,893,561 | B2 | 11/2014 | Gorjanc et al. |
| 9,186,479 | B1 | 11/2015 | Franceschetti et al. |
| 9,320,665 | B2 | 4/2016 | Main et al. |
| 9,659,322 | B2 | 5/2017 | Gorjanc et al. |
| 9,848,712 | B2 | 12/2017 | Main et al. |
| 9,860,982 | B2 | 1/2018 | Main et al. |
| 10,314,407 | B1 | 6/2019 | Main et al. |
| 10,562,412 | B1 | 2/2020 | Main et al. |
| 10,729,876 | B2 | 8/2020 | Main et al. |
| 10,973,344 | B2 | 4/2021 | Poodeh et al. |
| 2002/0155728 | A1 | 10/2002 | Khandros et al. |
| 2002/0184711 | A1 | 12/2002 | Mahoney et al. |
| 2003/0121101 | A1* | 7/2003 | Corzani ............... A47C 31/105 |
| | | | 5/699 |
| 2004/0133092 | A1 | 7/2004 | Kain |
| 2005/0012219 | A1* | 1/2005 | Liou .................. H01L 21/7682 |
| | | | 257/E21.579 |
| 2005/0165284 | A1 | 7/2005 | Gefen |
| 2005/0173144 | A1* | 8/2005 | Federighi .............. H01B 11/10 |
| | | | 174/27 |
| 2005/0241409 | A1 | 11/2005 | Taylor |
| 2007/0069642 | A1 | 3/2007 | Kitai et al. |
| 2007/0257821 | A1 | 11/2007 | Son et al. |
| 2008/0052837 | A1 | 3/2008 | Blumberg |
| 2008/0062176 | A1 | 3/2008 | Arya |
| 2008/0180390 | A1 | 7/2008 | Yoshikawa |
| 2008/0201856 | A1 | 8/2008 | Howard |
| 2008/0275349 | A1 | 11/2008 | Halperin et al. |
| 2009/0062693 | A1 | 3/2009 | Woolfson et al. |
| 2009/0070939 | A1 | 3/2009 | Hann |
| 2009/0093717 | A1 | 4/2009 | Carneiro et al. |
| 2009/0209830 | A1 | 8/2009 | Nagle et al. |
| 2009/0216466 | A1 | 8/2009 | Altman et al. |
| 2009/0240514 | A1 | 9/2009 | Oexman et al. |
| 2010/0022850 | A1* | 1/2010 | McKenna ............... A61B 5/002 |
| | | | 600/301 |
| 2010/0174198 | A1 | 7/2010 | Young et al. |
| 2010/0191541 | A1 | 7/2010 | Prokoski |
| 2010/0317930 | A1 | 12/2010 | Oexman et al. |
| 2010/0318239 | A1 | 12/2010 | Oexman et al. |
| 2011/0010014 | A1 | 1/2011 | Oexman et al. |
| 2011/0112442 | A1 | 5/2011 | Meger et al. |
| 2011/0245732 | A1 | 10/2011 | Mravyan et al. |
| 2011/0308019 | A1 | 12/2011 | Terawaki et al. |
| 2012/0296156 | A1 | 11/2012 | Auphan |
| 2012/0311790 | A1 | 12/2012 | Nomura et al. |
| 2013/0000047 | A1 | 1/2013 | McCann et al. |
| 2013/0006151 | A1 | 1/2013 | Main et al. |
| 2013/0090571 | A1 | 4/2013 | Nourani et al. |
| 2013/0144751 | A1 | 6/2013 | Gorjanc et al. |
| 2013/0283530 | A1* | 10/2013 | Main ..................... A47C 27/083 |
| | | | 5/600 |
| 2013/0332104 | A1 | 12/2013 | Russell |
| 2014/0288397 | A1 | 9/2014 | Sarrafzadeh et al. |
| 2014/0343889 | A1 | 11/2014 | Ben Shalom et al. |
| 2014/0366277 | A1* | 12/2014 | Niederkrom ....... A61G 7/05792 |
| | | | 5/652.2 |
| 2015/0320352 | A1* | 11/2015 | Ben Shalom ........ A61B 5/6892 |
| | | | 600/587 |
| 2015/0371522 | A1 | 12/2015 | Mravyan et al. |
| 2017/0281073 | A1 | 10/2017 | Drennan et al. |
| 2018/0027988 | A1 | 2/2018 | Poodeh et al. |
| 2018/0064402 | A1 | 3/2018 | Leydon |
| 2019/0026957 | A1 | 1/2019 | Gausebeck |
| 2020/0155059 | A1 | 5/2020 | Kayser et al. |
| 2020/0405217 | A1 | 12/2020 | Jayaraman et al. |

(56) References Cited

U.S. PATENT DOCUMENTS

| | | | |
|---|---|---|---|
| 2021/0196055 A1 | 7/2021 | Poodeh et al. | |
| 2022/0142834 A1 | 5/2022 | Hamilton et al. | |

FOREIGN PATENT DOCUMENTS

| | | | |
|---|---|---|---|
| CN | 101803983 A | 8/2010 | |
| EP | 2182339 A1 | 5/2010 | |
| FR | 2720622 A1 | 12/1995 | |
| JP | H04-325116 | 11/1992 | |
| JP | 2009-119082 A | 6/2009 | |
| WO | WO 01/00089 A1 | 1/2001 | |
| WO | WO 2009/102361 A1 | 8/2009 | |
| WO | WO 2010/045741 A1 | 4/2010 | |
| WO | WO 2011/066151 A1 | 6/2011 | |
| WO | WO 2011/091517 A1 | 8/2011 | |
| WO | WO 2012/160502 A1 | 11/2012 | |
| WO | WO 2013/085785 A1 | 6/2013 | |
| WO | WO 2014/145436 A1 | 9/2014 | |
| WO | WO-2015/002546 A1 | 1/2015 | |
| WO | WO-2019/178583 A1 | 3/2019 | |

OTHER PUBLICATIONS

PCT Invitation to Pay Additional Fees, PCT Application No. PCT/IB2021/000598, Jan. 5, 2022, two pages.
Bayer L., et al., "Rocking synchronizes brain waves during a short nap," Current Biology, 2011, pp. R461-R462, vol. 21, No. 12.
Fronczek, R., et al., "Manipulation of Core Body and Skin Temperature Improves Vigilance and Maintenance of Wakefulness in Narcolepsy," Sleep, 2008, pp. 233-240, vol. 31, No. 2.
Machiel Van Der Loos, H.F. et al., "Development of Sensate and Robotic Bed Technologies for Vital Signs Monitoring and Sleep Quality Improvement," Autonomous Robots, 2003, pp. 67-79, vol. 15.
Malakuti, K., "Towards an Intelligent Bed Sensor: Non-Intrusive Monitoring of Sleep Disturbances via Computer Vision Techniques," Thesis, University of Victoria, 2008, 93 pages.
Office Action for Chinese Patent Application No. CN 201180007313. 4, Dec. 31, 2013, 17 Pages.
PCT International Search Report and Written Opinion for PCT/IB2013/001276, Sep. 17, 2013, 7 Pages.
Raymann, R., et al., "Skin deep: enhanced sleep depth by cutaneous temperature manipulation," Brain, 2008, pp. 500-513, vol. 131.
Yousefi, R. et al., "A Smart Bed Platform for Monitoring & Ulcer Prevention," 2011 4$^{th}$ International Conference on Biomedical Engineering and Informatics (BMEI), IEEE, 2011, pp. 1362-1366.
Yousefi, R. et al., "Bed Posture Classification for Pressure Ulcer Prevention," 2011 Annual International Conference of the IEEE, Engineering in Medicine and Biology Society, EMBC, Aug. 30, 2011-Sep. 3, 2011, pp. 7175-7178.
A Good Mattress is a Dream Come True, New York Times News Service, Mar. 29, 1998, 1 page, available at http://articles.chicagotribune.com/1998-03-29/news/9803290437.sub.--1.sub-.--mattress-sleep-wake-disorder-center-bed.
amazon.com, "Honeywell Home RCHW3610WF1006/N Water Leak Detector," Apr. 20, 2018, nine pages, [Online] [Retrieved on Aug. 31, 2021] Retrieved from the Internet <URL: https://www.amazon.ca/Honeywell-RCHW3610WF1006-Water-Leak-Detector/dp/B07CJG91DM/ref=asc_df_B07CJG91DM/?tag=googleshopc0c-20&linkCode=df0&hvadid=292938317460&hvpos=&hvnetw=g&hvrand=9101712106439063987&hvpone=&hvptwo=&hvqmt=&hvdev=c&hvdvcmdl=&hvlocint=&hvlocphy=9001314&hvtargid=pla-554077522699&psc=1>.
Barhyte, et al., Selection of a Standard Hospital Mattress: Data-Based Decision Making, vol. 22, No. 6 Journal of Wound Ostomy & Continence Nursing, Nov. 1995, pp. 267-270, vol. 22, No. 6.
Brienza, et al., A Method for Custom-Contoured Cushion Design Using Interface Pressure Measurements, IEEE Transactions on Rehabilitation Engineering, Mar. 1999, pp. 99-108, vol. 7, No. 1.

Brienza, et al., Seat Cushion Optimization: a Comparison of Interface Pressure and Tissue Stiffness Characteristics for Spinal Cord Injured and Elderly Patients, vol. 79, Archives of Physical Medicine & Rehabilitation, Apr. 1998, pp. 388-394, vol. 79.
Chiradejnant, A., The Study of the Reliability and Validity of the Ergocheck Measurement System, School of Physiotherapy, University of South Australia, 1998. 74 pages.
Clark, M., "Comparison of the Pressure Redistributing Attributes of a Selection of Bed Mattresses Used to Prevent Pressure Sores," The Journal of Tissue Viability, Jul. 1991, pp. 65-67, vol. 1 No. 3.
Cork, Russel, "XSensor technology: A pressure imaging overview", Published in Sensor Review on 27.1 (2007): 24.; extracted for PQ dialog search on May 11, 2015.
Defloor, T. et al., "Sitting Posture and Prevention of Pressure Ulcers," Applied Nursing Research, Aug. 1999, pp. 137-142, vol. 12 No. 3.
Digi-Key, "Water Contact Indicator Tape," Date Unknown, three pages, [Online] [Retrieved on Aug. 31, 2021] Retrieved from the Internet <URL: https://www.digikey.ca/en/product-highlight/3/3m-tc/water-contact-indicator-tape>.
Ergocheck Brochure: Ergocheck Fulfils One of the Essential Demands of the Bedding Trade, ABW, 1994, 3 pages.
Ergocheck Measuring System, 1994 Ergocheck v.2.0 Reference Manual, 105 pages.
"Force Sensing Array Version 3.1 User Manual," 2 ed., Vista Medical Ltd., 1996, 66 pages.
Gignac, Tamara; "Xsensor's body maps guide manufacturers: Pressure-point technology has manyapplications"; [Final Edition] Publication info: Calgary Herald [Calgary, Alta] Mar. 13, 2006: B8.
Harstall, C., "Interface Pressure Measurement Systems for Management of Pressure Sores," Alberta Heritage Foundation for Medical Research, Sep. 1996, 21 pages.
Kreutz, D., Computerized Pressure Mapping, Advance for Directors in Rehabilitation, Nov. 11-12, 1997, 3 pages.
Krouskop, T.A. et al., "Factors Affecting the Pressure-Distributing Properties of Foam Mattress Overlays," Journal of Rehabilitation Research and Development, Jul. 1986, pp. 33-39, vol. 23, No. 3.
Lipka, D., "An Overview of Pressure-Mapping System," Technology Special Interest Section Quarterly, Dec. 1997, pp. 1-6, vol. 7 No. 4.
Malacaria, C., A Thin, Flexible, Matrix-Based Pressure Sensor, Sensors Magazine, Sep. 1998, 5 pages.
Nicol, K. et al., "Pressure Distribution on Mattresses," Journal of Biomechanics, 1993, pp. 1479-1486, vol. 26, No. 12.
Oxford Pressure Monitor, Operating Instructions (received by the Food and Drug Administration on Dec. 9, 1991), 32 pages.
Park, S.J. et al., "Measurement and Analysis of Pressure Distribution on the Bed," Proceedings of the Human Factors and Ergonomics Society 39.sup.th Annual Meeting, 1995, pp. 297-300.
Reswick, J.B. et al., Experience at Rancho Los Amigos Hospital with Devices and Techniques to Prevent Pressure Sores, in Bedsore Biomechanics 301, 307-08 (University Park Press 1976).
Reynolds, A. et al., Pressure-Reducing Capability of Conforma II Mattress Overlay, Advances in Wound Care, Jul. 1994, pp. 36-40, vol. 7, No. 4.
Rithalia, S. V.S. et al., "Assessment of Alternating Air Mattresses Using a Time-Based Interface Pressure Threshold Technique," Journal of Rehabilitation Research and Development, Jun. 1998, pp. 225-230, vol. 35 No. 2.
Shelton, et al., Full-Body Interface Pressure Testing as a Method for Performance Evaluation of Clinical Support Surfaces, Applied Ergonomics, 1998, pp. 491-497, vol. 29, No. 6.
SparkFun, "SparkFun Soil Moisture Sensor," Date Unknown, nine pages, [Online] [Retrieved on Aug. 31, 2021] Retrieved from the Internet <URL: https://www.sparkfun.com/products/13322>.
Talley Pressure Monitor 3, Operating Manual 1st Ed. Preliminary (received by the Food and Drug Administration on Dec. 9, 1991), 44 pages.
Telefax from A. Ahrens to L. Larson, Mar. 14, 1995, 1 page.
The Canadian Patient Safety Institute, "Never Events for Hospital Care in Canada," Sep. 2015, 11 pages, [Online] [Retrieved on Aug. 31, 2021] Retrieved from the Internet <URL: https://www.

(56) References Cited

OTHER PUBLICATIONS patientsafetyinstitute.ca/en/toolsResources/NeverEvents/Documents/Never Events for Hospital Care in Canada.pdf>.

Zabel, M., "Buying Mattresses for Comfort," University of Minnesota, 1969, 15 pages.

Bates-Jensen, B. M. et al., "Subepidermal Moisture Detection of Pressure Induced Tissue Damage on the Trunk: The Pressure Ulcer Detection (PUD) Study Outcomes," Wound Repair and Regeneration 25.3, May 2017, pp. 502-511.

United States Office Action, U.S. Appl. No. 17/339,401, May 8, 2023, 17 pages.

United States Office Action, U.S. Appl. No. 17/339,401, Sep. 20, 2023, 21 pages.

European Patent Office, Extended European Search Report and Opinion, EP Patent Application No. EP 21866152.8, Aug. 28, 2024, 11 pages.

\* cited by examiner

INTELLIGENT WEIGHT SUPPORT SYSTEM

TECHNICAL FIELD

The present disclosure generally relates to a weight support system, in particular to a weight support system that includes a sensor grid that can detect the sleep state of a person.

BACKGROUND

Sleep study, also referred to as polysomnography, may use various sensors to detect the bio-signals of the person who is in sleep. The sensors used may include electroencephalograms (EEG), pulse oximeters, respiratory belts, oronasal thermistors, and electrocardiograms (ECG). Typically, several of these sensors are used in combination. The recorded information is interpreted and scored by a trained individual who identifies the status of the person in sleep and may identify sleep disorders.

Unfortunately, many of the conventional sensors used in polysomnography are not portable, are disruptive to the user's sleep, and commonly require constant direct wiring to the user. This limits most polysomnography to be conducted in hospitals or specialized sleep labs. Also, the presence of the sensors often creates discomfort to the user and may affect the sleep quality of the user.

SUMMARY

Embodiments may relate to an air-permeable bedding system, which may include a microclimate fabric layer and an air-permeable capacitive sensor layer below the microclimate fabric layer. The air-permeable capacitive sensor layer may include two air-permeable substrates, each carrying a plurality of electrically conductive pathways that are impermeable to air. The two air-permeable substrates may securely position the electrically conductive pathways to define a sensor grid and position the electrically conductive pathways that are impermeable to air to be spaced apart to define a plurality of air pathways for the air-permeable capacitive sensor layer.

Embodiments may also relate to a computer-implemented process for determining the heart rate or the respiration rate of a person using a bedding system with a sensor grid. The process may include receiving pressure sensor data from the bedding system that includes the sensor grid that generates the pressure sensor data. The process may also include identifying, based on the pressure sensor data, a target body part of the person on the bedding system. The process may further include identifying a subset of the pressure sensor data generated from a region of the sensor grid that measures the pressure exerted by the target body part. The process may further include using the subset of the pressure sensor data to determine the heart rate or the respiration rate of the person.

Embodiments may further relate to a computer-implemented process for determining a sleep state of a person using a bedding system with a sensor grid. The process may include receiving a time series of pressure sensor data from the bedding system that includes the sensor grid that generates the pressure sensor data. The process may also include identifying the poses of a person on the bedding system based on the pressure sensor data. The process may also include determining respiration rates and heart rates of the person based on the pressure sensor data. The process may further include inputting the poses, the respiration rates, and the heart rates of the person to a machine learning model to determine a sleep state of the person.

BRIEF DESCRIPTION OF THE DRAWINGS

Figure (FIG. 1 is a block diagram illustrating an example system environment of a weight support system, according to some embodiments.

Figure 1:
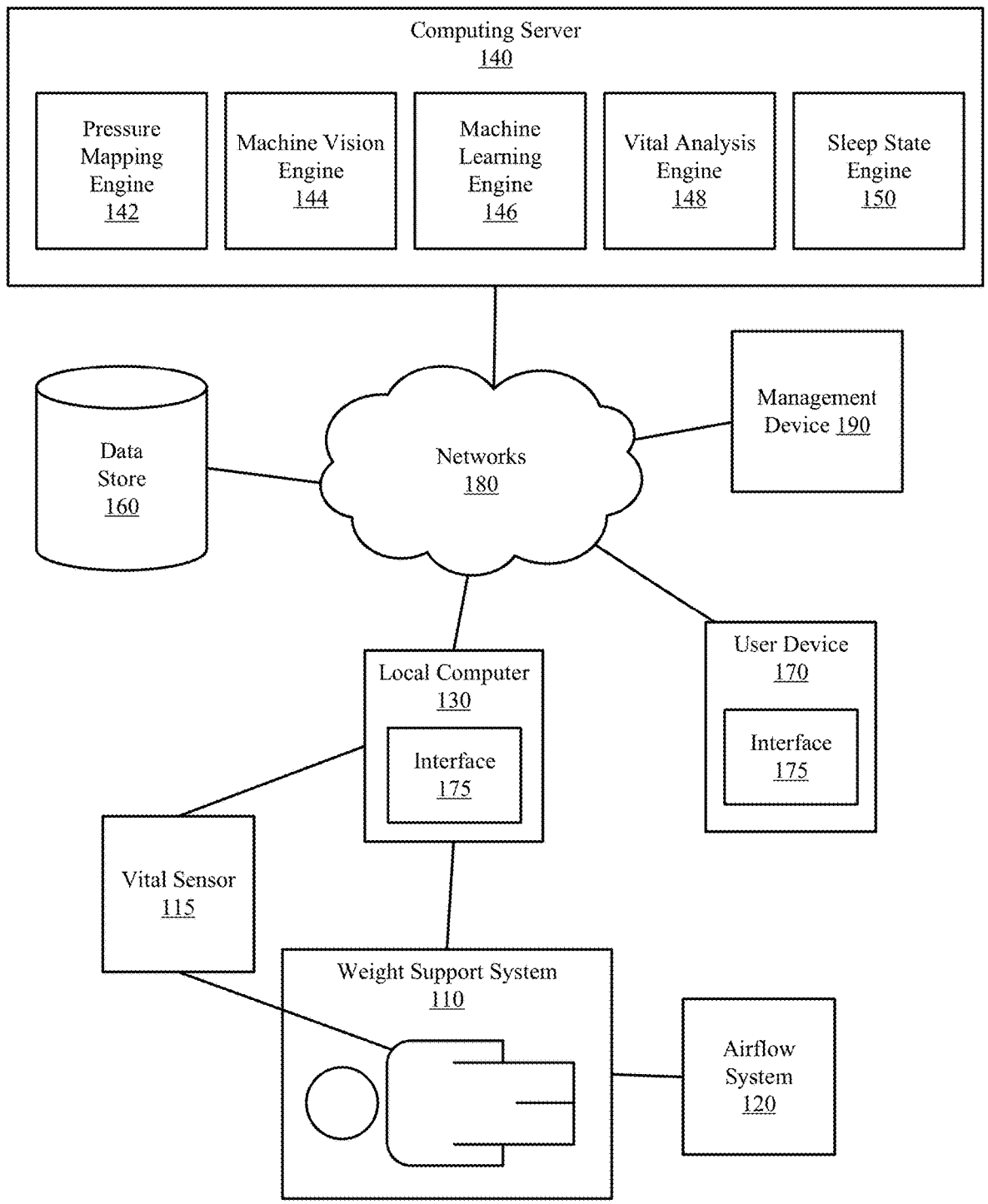

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

Embodiments described herein relate to a weight support system, which may be referred to as an intelligent sheet (or surface), for wireless monitoring of pressure, vital signs, and a variety of other useful clinical information. The intelligent surface may take the form of a portable and flexible mat that can provide biometric information without any direct wiring connected to the user. In some embodiments, the intelligent surface simply serves as a pad or a support layer for the user to sleep, sit, or otherwise rest. The system may include a fitted sheet, mattress, overlay, or topper with an embedded capacitive pressure sensor layer, which may be combined with other sensing technologies including piezoelectric sensors, accelerometers, thermistors, or others. Embodiments described are also related to methods of constructing the permeable capacitive pressure grid sensor layer that may be used as the embedded capacitive pressure sensor in the weight support system.

By way of example, the main sensor may be a thin and flexible capacitive pressure sensor grid layer that includes two types of electrodes: columns, where a sinusoidal electrical signal may be injected; and rows, where an attenuated sinusoidal signal may be detected. The electrodes are separated by a compressible dielectric material. When the material is compressed by the weight from the user, the injected electoral signal is attenuated as it passes through the dielectric. The attenuation is measured by sensor electronics. By arranging these sensels, or electrode pairs, on a sensor mat, a matrix of pressure values can be captured.

Alternative or additional sensing technologies that may be used in the weight support system include piezoelectric sensors, accelerometers, electrodes, resistive pressure sensors, and thermistors. The signals from these sensors can supplement the information provided by the matrix of pressure values to provide richer information for use in the sleep state detection system.

In accordance with some embodiments, several signal processing techniques and machine learning models are used to detect sleep state, body movement, respiration rate, heart rate, body/joint/limb position, activity level, seizures, surface/bed occupancy, fall probability, respiration/heart failure, and other activities such as speaking, coughing, eating, and drinking. Biometrics that can be derived from the signals of the intelligent surface may include but are not limited to body position, the positions of joints, movement monitoring, respiration rate, heart rate, and sleep state. The intelligent surface may be associated with an artificial intelligence system, which may use multiple types of machine learning models to identify the individual's biometric signals. Several novel processing techniques allow for the intelligent surface to identify sleep state with a minimally disruptive setting.

In some embodiments, for the sleep state detection, a computer may receive the raw pressure frame generated from the embedded capacitive pressure sensor layer and generate respiration rate signal, and heart rate signal, along with their respective extracted features and information from additional sensors. The features, along with some biometrics generated, such as positions of joints and movement data, may be fed into a system that uses machine learning models to automatically determine if the user is awake or in one of the following sleep states such as N1, N2, N3, or REM sleep.

Example System Environment

Referring now to Figure (FIG. 1, shown is a block diagram illustrating an embodiment of an example system environment 100 of a weight support system 110, in accordance with some embodiments. By way of example, the system environment 100 includes a weight support system 110, a vital sensor 115, an airflow system 120, a local computer 130, a computing server 140, a data store 160, a user device 170, a management device 190, and networks 180. In various embodiments, the system environment 100 may include fewer or additional components. The system environment 100 also may include different components. Also, while some of the components in the system environment 100 may sometimes be described in a singular form, the system environment 100 may include one or more of each of the components.

The weight support system 110 may include layers that support the weight or part of the weight of a person and include sensors that monitor the status of the person. Examples of the weight support system 110 include a bedding system, a seating system, a sheet, a cushion, a pillow, a pad, etc. The weight support system 110 may also be referred to as an intelligent surface. While in this disclosure the weight support system 110 is often described as a bedding system, various features and components of the bedding system may also be applied to other types of the weight support system 110 without explicitly referred to those types of the weight support system 110. The weight support system 110 may come in various sizes and different forms. For example, a bedding system may be an intelligent mattress that may include various comfort layers such as foam. In another example, a bedding system may be a pad that is intended to complement a conventional mattress (e.g., being laid on top of the mattress). A bedding system may also be used in a special setting such as in the hospital or senior care facility. The weight support system 110 may also be a seating system that can be used as an intelligent office seat that monitors the posture of a person, a car seat (or a cushion for a car seat), or a wheelchair seat. Other examples of the weight support system 110 are also possible.

The weight support system 110 may include one or more types of sensors that are used to monitor the status and certain vital information of the person sleeping, seating, or otherwise resting on the weight support system 110. The sensors may include a pressure sensor grid that includes an array of pressure sensing elements. The pressure sensing elements may take the form of resistive pressure sensors, fiber-optic pressure sensors, or capacitive pressure sensors. The weight support system 110 may also include other types of sensors such as piezoelectric sensors, accelerometers, and thermistors. The weight support system 110 may be intended to support a single person or multiple persons. For example, in a bedding system, a first embodiment of the weight support system 110 may support the acquisition of data of a single person. A second embodiment of the weight support system 110 may simultaneously acquire data for two or more people, such as in the situation of a larger mattress.

The weight support system 110 may include various comfort features such as one or more microclimate fabric layers that may be used to regulate the humidity, airflow, and temperature of the surface of the weight support system 110. The pressure sensor grid may also be formed from air permeable materials so that the pressure sensor grid layer is also air permeable. The weight support system 110 may also include a comfort layer that adjusts the firmness of the system. Structures and various components of different embodiments of the weight support system 110 will be discussed in further detail with reference to FIG. 2A through FIG. 3B.

The weight support system 110 may further include an inlet that can be connected to an active air source such as the airflow system 120 to enhance the air circulation and flow inside the weight support system 110. For example, the airflow system 120 may be a fan or a pump that moves air into some of the inner layers of the weight support system 110. In turn, the air is circulated through the air-permeable layers to exit the weight support system 110 through its surfaces. The airflow system 120 may be computer-controlled based on readings from temperature sensors and humidity sensors installed at the weight support system 110 to actively regulate the microclimate of the system. The weight support system 110 may also include various accessory devices such as temperature control devices, temperature sensors, white noise generators, audio sensors, biofeedback sensors, lighting controls, and light sensors. Communication and control of the accessory devices can be performed via a Universal Serial Bus (USB) port, Firewire port, or via Bluetooth or WiFi wireless connections. Some example additional comfort features are discussed in U.S. Patent Application Publication 2018/0027988, dated Feb. 1, 2018, entitled "Bedding System with a CNN Based Machine Vision Process," which is incorporated by reference herein for all purposes.

The weight support system 110 may generate sensor signals and be in communication with a computer to automatically detect the sleep state of the person. The weight support system 110 may take the form of a portable flexible mat that can provide biometric information without any direct wiring connected to the user. The weight support system 110 may measure the pressure exerted by the person using a sensor grid to generate a matrix of pressure readings. The matrix of pressure readings, which may be supplemented with other supporting sensors, may be provided to a computer with an artificial intelligence system which uses multiple types of machine learning networks (a convolutional neural network (CNN), a long short term memory (LSTM) network, etc.) to identify the person's biometric signals. Biometrics deduced based on signals provided by the weight support system 110 may include, but are not limited to, body position, the position of joints, movement monitoring, respiration rate, heart rate, and sleep state. Several data processing and machine learning techniques that will be discussed in further detail below with reference to FIG. 5A through 9 can identify sleep state with a minimally disruptive sensing system such as the weight support system 110.

The person on the weight support system 110 may also be monitored by one or more vital sensors 115 that measure the person's vitals such as heart rate, respiration rate, body temperature, blood pressure, blood sugar level, etc. Depending on embodiments, the vital sensors 115 may be part of the weight support system 110 or independent devices. For example, in one embodiment, the weight support system 110 is equipped with sensors that can detect the heart rate, respiration rate, and body temperature. In another embodiment, the heart rate may be detected through an external vital sensor 115 that is not part of the weight support system 110. For example, the external vital sensor 115 may be a chest strap or wrist band electrocardiographic device that is used to measure electrical heart information. The sensors 115 may also be professionally graded or customer graded. For example, in a hospital setting, the weight support system 110 may be used as a hospital bed for a patient who is monitored by different kinds of medically graded vital sensors 115. In another example, one of the vital sensors 115 may simply be a wearable electronic device such as APPLE WATCH or a FITBIT smartwatch. For example, the heart rate of the person may be input from an external device that is embedded into the weight support system 110 or attached to the person outside of the weight support system 110. The sensors 115 may also include a pulse oximeter.

In some embodiments, the weight support system 110 and the vital sensor 115 may be connected to a local computer 130 that is located, for example, in the same place of the weight support system 110. In some embodiments, the weight support system 110 may be equipped with processing power such as having built-in CPUs or the local computer 130 being part of the weight support system 110. In other embodiments, the local computer 130 may be a separate computer that connects to the weight support system 110 and the vital sensor 115 to collect data from those devices. The local computer 130 may upload the data via networks 180 to the computing server 140 for further processing. In some embodiments, the local computer 130 may also have the software installed to analyze the data from the weight support system 110 or the vital sensor 115. For example, in a hospital setting, the local computer 130 may be a bedside monitor that provides analyses of various data in real-time and display the vitals of the patient. In other embodiments, the local computer 130 simply collects data or performs certain data processing (such as compression, conversion of formats) for the computing server 140 to further analyze the data. The role of the local computer 130 may vary in different implementations and settings. In some embodiments, local computer 130 may not be present. For example, the weight support system 110 may be equipped with a wireless capability that can directly transmit its data to the computing server 140 for processing.

In some embodiments, a weight support system 110 (or a computer that processes the raw data of the weight support system 110) may transmit data such as visual feedback of motions and positions, other vital signs such as temperature, oxygen level heart rates and respiration rate, in a secure network environment to the user and to a management dashboard (e.g., at a nursing station or front management desk in a retirement home) of a management device 190 to highlight the state and status of all subjects being monitored with the added element of an alert system should there be any trends or behavior outside of preestablished parameters (e.g., oxygen level).

The computing server 140 may be a remote server that is used to analyze data collected from the weight support system 110 and the vital sensor 115 to determine the status and biometrics of the person on the weight support system 110. The computing server 140 may take the form of a combination of hardware and software, such as engines 142 through 150. The computing server 140 may include some or all example components of a computing machine described with FIG. 9. The computing server 140 may take different forms. In one embodiment, the computing server 140 may be a server computer that executes code instructions to cause one or more processors to perform various processes described herein. In another case, the computing server 140 may be a pool of computing devices that may be located at the same geographical location (e.g., a server room) or be distributed geographically (e.g., clouding computing, distributed computing, or in a virtual server network). The computing server 140 may also include one or more virtualization instances such as a container, a virtual machine, a virtual private server, a virtual kernel, or another suitable virtualization instance.

The computing server 140 may include various algorithms for data analysis. The pressure mapping engine 142 may perform basic functions such as data messaging with the sensors, conversion of measurements from the sensors to calibrated pressure values, and organization of data into an array of measurements representative of the sensor array. The pressure mapping engine 142 may also operate in a non-calibrated mode where raw pressure sensor measurements are compared and processed relative to other raw pressure sensor measurements and absolute pressure values are not calculated. An example of an array of pressure measurements, shown in FIG. 5C, includes a two-dimensional pressure image of a person. This may be a graphical representation of the measurement information that is generated and stored by the pressure mapping engine 142. Areas of low-pressure measurements are shown in darker shades. The pressure mapping engine 142 may also calculate a number of parameters that are derived from the pressure image. For example, the contact area can be calculated for the entire pressure sensing area. The contact area is based on the number of sensing points with measured pressure above a minimum threshold.

In another example, average peak pressure can be calculated over the entire pressure sensing area. In one approach, the average peak pressure is calculated by isolating a group of sensing points with the highest measured pressures (the peak pressures), then averaging those pressure values to obtain the result. A sensing point is an individual sensing element within the sensor array. For example, using a bed sensor with 1664 sensing points in the sensor area, the 16 sensing points with the highest pressure measurements could be averaged to determine the average peak pressure. The number of sensing points averaged could be 25% to 0.5%, or preferably 1%, of the total number of sensing points in the array. The number of sensing points averaged could also be 25% to 0.5%, or preferably 1%, of the total number of sensing points in the array that are above a pressure threshold, for example, 10 mmHg. The average peak pressure algorithm may also reject peak pressures to reduce the impact of creases in the sensor, objects in the customer's pockets, or hard edges in the customer's clothing. For example, the one to ten, or preferably three, highest pressure measurements can be excluded from the average peak pressure calculation.

Other pressure-related parameters can also be calculated from the sensor data. For example, a load calculation could be used to estimate a person's weight. The person's height can be estimated by adding the number of sensing points above a minimum pressure from the person's head to their toes when they are lying on their back. Shear forces can also be estimated based on the pressure gradient between sensing points. In another example, pressure data can be used to analyze the distribution of pressure over the entire sensing area.

The pressure data and related metrics may be further processed by the machine vision engine 144, machine learning engine 146, vital analysis engine 148, and sleep state engine 150.

The machine vision engine 144 analyzes pressure data to identify body types and to identify body position. Machine vision engine may include one or more algorithms (which could include AI or not) that extracts features from the pressure image. When a person first lies on a two-person weight support system 110 (a bedding system), the machine vision engine 144 analyzes the two-dimensional pressure image of the sleeper and derives a physical profile. The physical profile is matched to the two physical profiles stored during the setup process of the bedding system. The machine vision process determines the identity of the person entering the bed and passes this information to other components. The bedding system can then be configured appropriately for that person.

A "physical profile" is at least one physical attribute of individuals which can be derived from the pressure sensor dataset acquired from a reference mattress. The physical profile may include attributes such as measurements of certain body features, for example, height, weight, shoulder-width, hip-width or waist-width; or ratios of these measurements, for example, shoulder to hip ratio, shoulder to waist ratio, or waist to hip ratio; body type, for example, endomorph, ectomorph, endomorph; or Body Mass Index (BMI).

In another example, a peak pressure curve is created along the length of a person lying on their back or side. A mass distribution may be calculated from applied pressure over a given unit area. For example, a mass can be calculated for each individual sensing point in the sensing array by multiplying the measured pressure by the area of the sensing point. Mass can also be calculated for larger areas by averaging pressure measurements over a group of sensing points, for example, 2×2 or 4×4 sensing points. A body mass curve can also be created along the length of a person lying on their back or side. A peak pressure curve and/or a body mass curve can also be used for matching a body profile.

The machine learning engine 146 uses the pressure data to detect the sleep states, poses and other biometrics of the person. The changes in pressure may indicate movement or restlessness. For example, if the pressure sensing points above a minimum pressure threshold show little variation over a period of time, then the person can be considered as motionless. A variation threshold of 10% to 100% of the measured pressure can be used to determine if there is movement on a particular sensing point or group of sensing points. The machine learning process tracks periods of stillness and movement to create a person's sleep profile for the night. Major position changes are detected by the machine vision engine 144 and these can also be tracked to determine if a person has been tossing and turning throughout the night. Details of the identification of the sleep state and the pose of a person are further discussed with reference to FIG. 6A through FIG. 6D.

The machine learning engine 146 continuously monitors and processes the pressure data to determine a person's body position. For example, position classifications can include "on back," "left side," or "right side." The machine learning engine 146 may also determine the positions of joints of the person and the movement of the person. Details of the visioning process are further discussed with reference to FIG. 6A through FIG. 6D.

The vital analysis engine 148 analyzes data from the weight support system 110 and the vital sensor 115 to determine one or more biometrics that describe the vitals of the person. For example, the vital analysis engine 148 may rely on the machine learning engine 146 and the machine vision engine 144 to determine a target body part of the person. The vital analysis engine 148 may focus on the sensor data associated with the target body part to determine certain vital information of the person. Details of the vital analysis of a person are further discussed with reference to FIG. 5A through FIG. 5B.

The sleep state engine 150 may be part of the machine learning engine 146 and may use pressure data and data from the machine vision engine 144, the machine learning engine 146, and the vital analysis engine 148 to assess the state of a person's sleep. For example, bed entry can be detected when the pressure data changes from no pressure to a pressure indicating that there is a person on the bed. The "bed empty" state is detected when a threshold number of sensing points are below a threshold pressure value. For example, if a vast majority of sensing points (e.g., 90%, 98%, 100%, or a predetermined threshold level set by the designer) measure pressure below 1 mmHg to 20 mmHg, or preferably 5 mmHg, then the sleep state is "bed empty." A transition from the "bed empty" state to "bed entry" state indicates that a person has gotten into bed.

An example of a sleep state sequence may show a person transitioning between "bed entry," "still", and "restless" states with corresponding body positions determined by the machine vision engine 144. The sleep state information may be passed to the weight support system 110 that initiates adjustments to the support and comfort attributes of the adjustable mattress. For example, in the "bed entry" and "restless" states, the amount of support can be reduced and comfort increased to induce sleep. Support can be compromised in favor of comfort until a restful sleep is restored. In the "still" state, support is increased even if it results in a reduction in comfort. This is to ensure the best spinal alignment during deep sleep. In the "awaken" state, the support and comfort attributes can be adjusted such that sleep is inhibited, for example, the adjustable mattress can be made extra firm.

The sleep state engine 150 can utilize pressure data or other sensors to detect the accepted standard 5 states of sleep: stage 1, transition stage between sleeping and waking where the brain produces high amplitude theta waves; stage 2, the body prepares to enter deeper sleep where brain waves become slower and bursts of rapid, rhythmic brain wave activity known as sleep spindles occur, body temperature starts to decrease and heart rate begins to slow; stage 3, transitional state between light and deep sleep, slow brain waves known as delta waves begin to occur; stage 4, deep sleep where delta waves occur; stage 5, Rapid Eye Movement (REM) sleep, characterized by eye movement, increased respiration and increased brain activity. Micro changes in pressure can be analyzed to detect changes in respiration or a brain wave sensing headband could be worn to detect the beta, alpha, theta and delta waves associated with the 5 stages of sleep.

Sleep state or sleep stage information can be passed to the machine learning engine 146 to compare the night's sleep to previous or average patterns recorded. This information can be used to assess the performance of the support and comfort attribute adjustments implemented through the night.

The data store 160 includes one or more storage units such as memory that takes the form of non-transitory and non-volatile computer storage medium to store various data that may be uploaded by the local computer 130 or directly by the weight support system 110. The data stored in data store 160 may include sensor data and other data captured by the weight support system 110 and also analysis results generated by the computing server 140, such as the historical sleep state data and biometric data. The computer-readable storage medium is a medium that does not include a transitory medium such as a propagating signal or a carrier wave. The data store 160 may take various forms. In one embodiment, the data store 160 communicates with other components by the networks 180. This type of data store 160 may be referred to as a cloud storage server. Example cloud storage service providers may include AWS, AZURE STORAGE, GOOGLE CLOUD STORAGE, etc. In another embodiment, instead of a cloud storage server, the data store 160 is a storage device that is controlled and connected to the computing server 140. For example, the data store 160 may take the form of memory (e.g., hard drives, flash memories, discs, ROMs, etc.) used by the computing server 140 such as storage devices in a storage server room that is operated by the computing server 140.

The user device 170 may be used by a device that is possessed by the person on the weight support system 110. Examples of user devices 170 include personal computers (PCs), desktop computers, laptop computers, tablet computers, smartphones, wearable electronic devices such as smartwatches, or any other suitable electronic devices. The user device 170 may include an application such as a software application provided by the computing server 140. The application may provide various results and analyses of the data collected by the weight support system 110 and vital sensor 115 and may also allow the person to adjust various settings associated with weight support system 110, such as the airflow system 120. An application may be of different types. In one case, an application may be a web application that runs on JavaScript, etc. In the case of a web application, the application cooperates with a web browser to render a front-end interface 175. In another case, an application may be a mobile application. For example, the mobile application may run on Swift for iOS and other APPLE operating systems or on JAVA or another suitable language for ANDROID systems. In yet another case, an application may be a software program that operates on a desktop computer that runs on an operating system such as LINUX, MICROSOFT WINDOWS, MAC OS, or CHROME OS.

An interface 175 may be a suitable interface for a user device 170 to interact with computing server 140. The interface 175 may include various visualizations and graphical elements to display information for users and may also include input fields to accept inputs from users. A user may communicate to the application and the computing server 140 through the interface 175. The interface 175 may take different forms. In one embodiment, the interface 175 may be a web browser such as CHROME, FIREFOX, SAFARI, INTERNET EXPLORER, EDGE, etc. and the application may be a web application that is run by the web browser. In another application, the interface 175 is part of the application 122. For example, the interface 175 may be the front-end component of a mobile application or a desktop application. The interface 175 also may be referred to as a graphical user interface (GUI) which includes graphical elements to display a digital map and excavation-related information. In another embodiment, the interface 175 may not include graphical elements but may communicate with the computing server 140 via other suitable ways such as application program interfaces (APIs).

The various functionalities of the computing server 140 may also be performed by the local computer 130 or the user device 170, depending on the implementation and configuration. For example, the software algorithms that perform the various process associated with engines 142, 144, 146, 148, and 150 in the computing server 140 may also reside in the local computer 130 or a mobile application of the user device 170 so that the local computer 130 or the user device 170 may directly analyze the data generated by the weight support system 110. Results generated may be displayed at the user device 170, at the local computer 130, or at both devices. The computing server 140 may manage a mobile application that can cause the local computer 130 or the user device 170 to generate a user interface 175 that displays various results, predictions, determinations, and graphical illustrations of sensor data generated by the weight support system 110. In some embodiments, the weight support system 110 may also include computing components and software for analyzing the data directly and display the results.

The networks 180 provide connections to the components of the system environment 100 through one or more sub-networks, which may include any combination of the local area and/or wide area networks, using both wired and/or wireless communication systems. In one embodiment, the networks 180 use standard communications technologies and/or protocols. For example, a network 180 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 180 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 180 may be represented using any suitable format, such as hypertext markup language (HTML), extensible markup language (XML), JavaScript object notation (JSON), structured query language (SQL). In some embodiments, all or some of the communication links of a network 180 may be encrypted using any suitable technique or techniques such as secure sockets layer (SSL), transport layer security (TLS), virtual private networks (VPNs), Internet Protocol security (IPsec), etc. The networks 180 also include links and packet switching networks such as the Internet.

Example Weight Support System Configurations

Figure 2A:
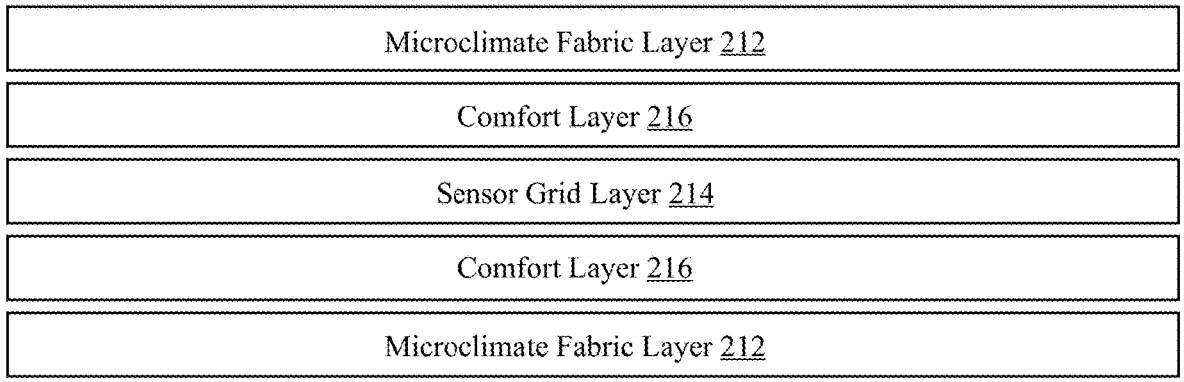
FIGS. 2A, 2B, and 2C are block diagrams illustrating cross-sectional views of various example configurations of weight support systems, in accordance with some embodiments.
Figure 2B:
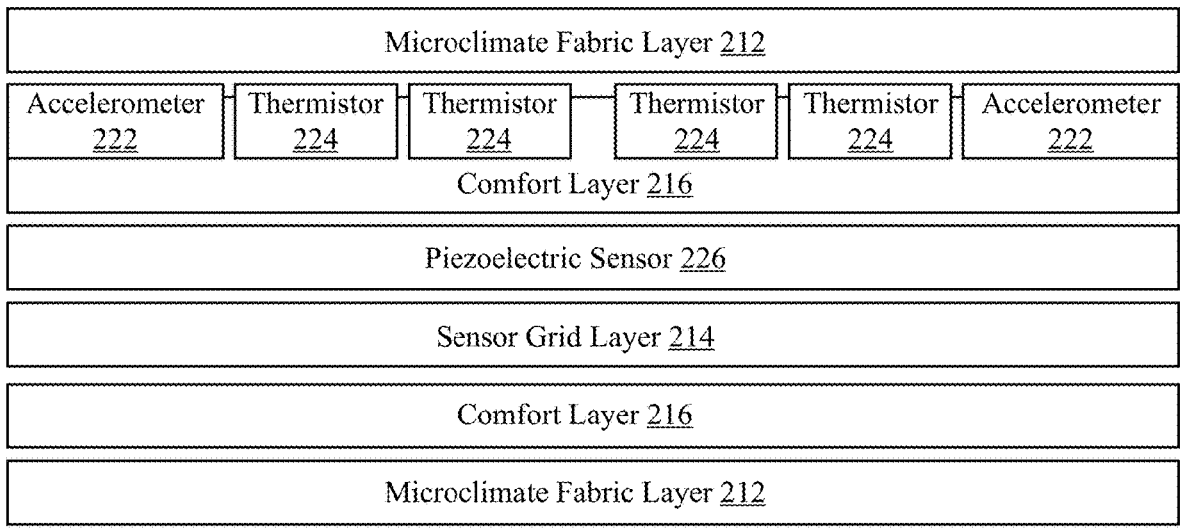
Figure 2C:
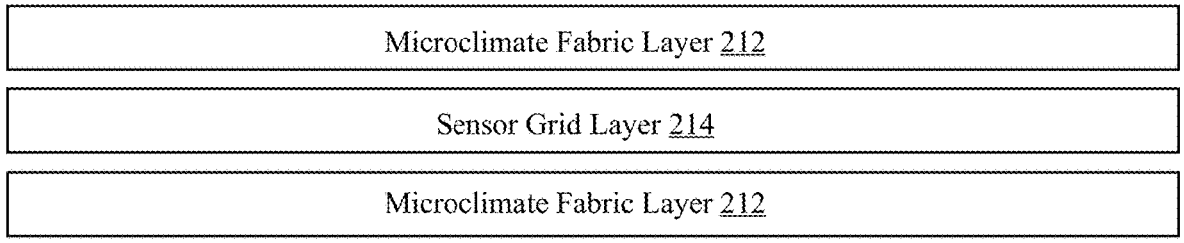

FIGS. 2A, 2B, and 2C are block diagrams illustrating cross-sectional views of various example configurations of weight support systems, in accordance with some embodiments. The weight support systems 210, 220, and 230 are examples of the weight support system 110 shown in FIG. 1. The configurations and layers shown in FIG. 2A through FIG. 2C are for example only. In various embodiments, a weight support system may include different, fewer, or additional layers. Certain orders of the layers may also be changed. Furthermore, the layer configuration in one example may be combined with that in another example. Depending on embodiments, the weight support system may be one-sided or two-sided. One or more layers may be removable from the weight support system for washing and cleaning. Also, while in FIG. 2A through FIG. 4B many example embodiments discussed herein have air-permeable structure or features, an embodiment of the weight support system 110 may also be not air-permeable or some of the air-permeable structure may not be present.

Referring to FIG. 2A, the weight support system 210 includes microclimate fabric layers 212 as outer layers, a sensor grid layer 214 as a middle layer, and one or more comfort layers 216 that may be used to sandwich or cover the sensor grid layer 214. The entire weight support system 210 may be wrapped by one or more microclimate fabric layers 212.

A microclimate fabric layer 212 may provide regulation to microclimates such as moisture, air, heat, cooling, humidity to the weight support system 210, particularly for the microclimate that may be formed between its surface and the skin of a person. For example, the microclimate fabric layer 212 may be used to reduce the skin temperature and limit the skin's moisture level. The microclimate fabric layer 212 may be a layer that is intended to be directly in contact with the person. The microclimate fabric layer 212 may be medical-graded. The fabric used may be air permeable and washable. The fabric may be formed from suitable materials such as polyester, polyamide, or a composite fabric. To further reduce build-up of moisture, the fabric may be coated with a water-resistant material.

The comfort layer 216 may be formed from foam or other suitable materials that may be used in mattresses, cushions, or seats. The comfort layer 216 may be located below the microclimate fabric layer 212 and above the sensor grid layer 214 to serve as a cushion layer to reduce the potential discomfort brought by the sensor grid layer 214 that might include more rigid components. The material and the thickness of the comfort layer 216 may be selected based on the sensitivity of the sensor grid layer 214. Although the comfort layer 216 may reduce the sensitivity of the sensor grid layer 214, the material of the comfort layer 216 selected should allow the sensor grid layer 214 to perform measurements such as pressure that are related to the person. Also, in some embodiments, to make the entire weight support system 210 air permeable, air-permeable material such as foam may be selected. The thickness of the comfort layer 216 may also be adjusted based on a balance of the comfort provided by the comfort layer 216 and the sensitivity of the sensor grid layer 214.

The sensor grid layer 214 includes one or more sensor grids, which may include a plurality of sensing points distributed in a target area or substantially the entire surface of the weight support system 210 for taking measurements at different locations. The sensor grid layer 214 may include a pressure sensor grid that includes an array of pressure sensing elements. The pressure sensing elements may take the form of resistive pressure sensors, fiber-optic pressure sensors, or capacitive pressure sensors. In some embodiments, the sensor grid layer 214 may have a configuration that makes the sensor grid layer 214 air permeable. An example of the configuration of the sensor grid layer 214 will be discussed in further detail below with reference to FIG. 3A through 3B.

In one example embodiment, the sensor grid layer 214 may take the form of a thin and flexible capacitive pressure sensor that includes two types of electrodes: columns and rows. Sinusoidal electrical signals are injected at the column electrodes while attenuated sinusoidal signals are detected at the row electrodes, or vice versa. The layer of column electrodes and the layer of row electrodes may be separated by a compressible dielectric material. As a result of the material being compressed by the weight of the user, the injected electoral signal is attenuated as the signal passes through the dielectric. The attenuation is measured by sensor electronics. A plurality of sensing points that may be formed at the intersections of the column and row electrodes. By arranging the sensing points on a sensor mat, a matrix of pressure values can be captured.

Referring to FIG. 2B, a second example of a weight support system is illustrated. The weight support system 220 may include additional layers and sensors compared to the weight support system 210. The weight support system 220 may include one or more accelerometers 222, one or more thermistors 224, and a piezoelectric sensor 226. The accelerometers 222 and the thermistors 224 may be located above the comfort layer 216 so that the sensors are closer to the person. The accelerometers 222 may be used to monitor the movement of the person. The movement data generated by the accelerometers 222 may be used to deduce certain vital measurements such as the heart rate and the respiration rate. The movement data may also be used to deduce the person's condition, such as the person's sleep condition. The thermistors 224 may be used to directly measure the person's skin temperature or serve as proxies to measure the person's temperature. The piezoelectric sensor 226 may also take the form of a sensor grid and may be used as another pressure sensor that is specialized in making certain measurements. For example, the piezoelectric sensor 226 may be specialized in generating pressure data that can be used to deduce the person's heart rates. On the other hand, the sensor grid layer 214 may generate sensor data that is used to deduce other biometrics, such as respiration rates, and other poses.

In some embodiments, the signals from the additional sensors shown in the weight support system 220 can supplement the information provided by the matrix of pressure values generated by the sensor grid layer 214 to provide richer information for use in the sleep state detection system. A piezoelectric sensor 226 may have substantially better dynamic responses compared to capacitive pressure sensing technology that may be used in the sensor grid layer 214. While the piezoelectric sensor 226 may respond to fluctuations in pressure, it may be extremely sensitive to the noise produced by body movements and have no capability of monitoring static pressure. Both capacitive and piezoelectric pressure sensors can be used in the weight support system 220 to allow for the monitoring of both highly dynamic signals (such as heart rate) and static surface pressure and body movements.

Figure 2D:
FIG. 2D is a conceptual diagram that shows several example top views of various weight support systems, in accordance with some embodiments.

FIG. 2D is a conceptual diagram that shows several example top views of various bedding systems to illustrate example positions of various sensors locations, in accordance with various embodiments. The sensor grid layer 214 may be located throughout substantially the entire surface of the bedding system. The piezoelectric sensor 226 may be specialized in measuring the heart rates of the person and may be located in the area that corresponds to the person's main body, such as the chest area. For example, in one embodiment, the piezoelectric sensor 226 may be located in the area, lengthwise, between 20% of the length and the midpoint of the length. The accelerometers 222 may be located at the corners of the bedding system to monitor the movement of the person. The thermistors 224 may be distributed throughout the area of the bedding system to measure the body temperatures at different parts of the person. The distribution may be uniform or may be more concentrated in particular target areas. The positions of the sensors may change based on the type of weight support systems. For example, in a seating system, the piezoelectric sensor 226 may be located at the back support of the seating system.

The structure of the weight support system can be changed to meet the implementation needs. For example, for short term monitoring applications, the structure of the weight support system can be simplified to just the microclimate fabric layer 212 and the sensor grid layer 214, as illustrated in FIG. 2C as the weight support system 230. The simplification of the weight support system 230 may reduce the cost of manufacturing and also reduce the thickness of the system for easier storage. For a longer-term but basic monitoring, such as in household situations where end users would like to monitor their day-to-day sleep conditions, body position, the position of joints, movement monitoring, and respiration rate, the sensor grid layer 214 may be used (or, in some situations, with the addition of the piezoelectric sensor 226). The more simple weight support system 210 may be used in these situations. For more complex and long-term monitoring applications, such as in intensive care situations or in other hospital settings, where various biometrics may need to be monitored, the addition of supplementary sensors such as accelerometers 222, thermistors 224, and external vital sensors 115 may be used to supplement the weight support system 220.

Figure 2E:
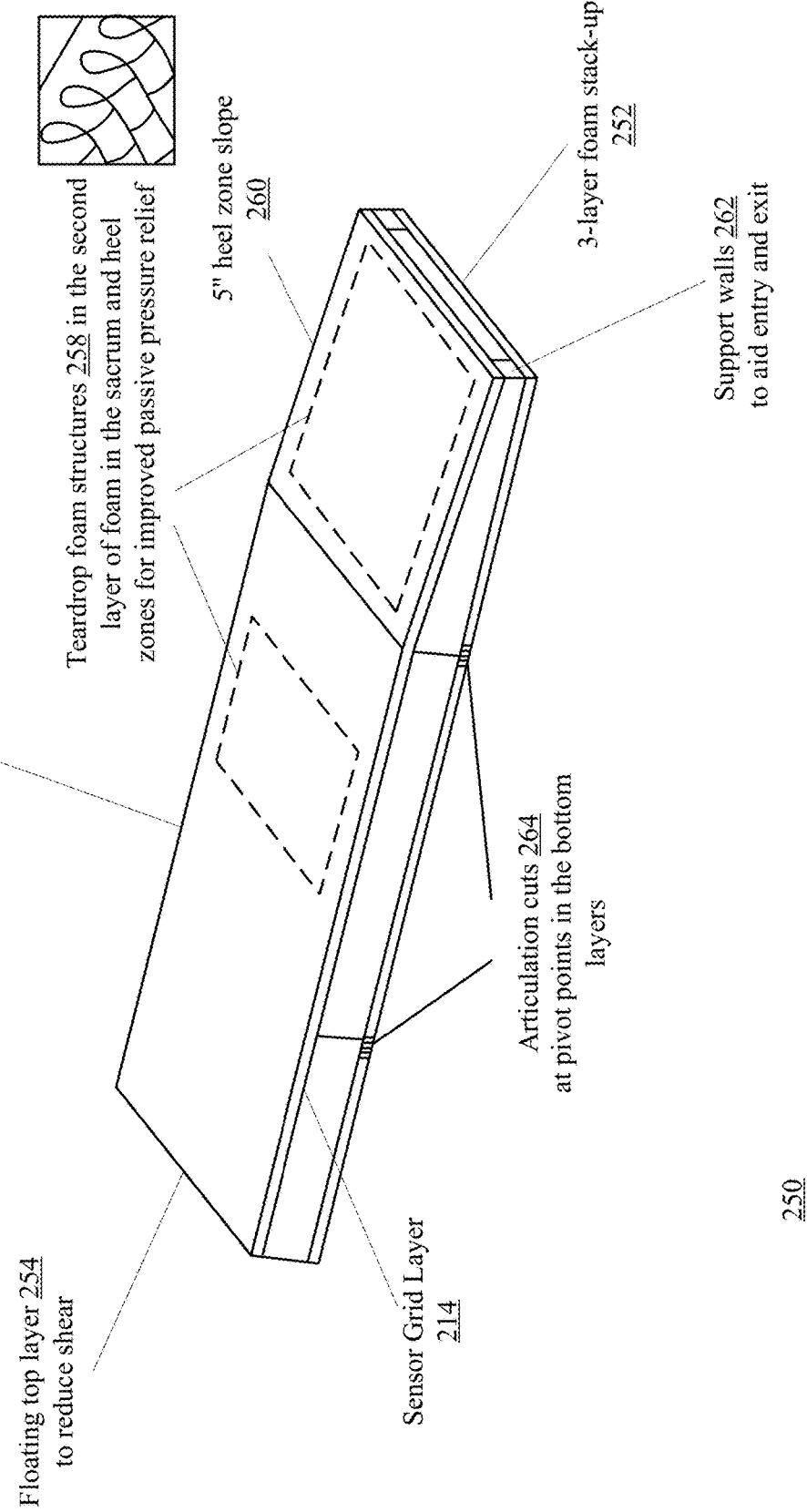
FIG. 2E is a perspective view of an example weight support system, in accordance with some embodiments.

FIG. 2E is a perspective view of an example weight support system 250 that illustrates one or more additional features that may or may present in various implementations, in accordance with some embodiments. The weight support system 250 may be an example of the weight support system 110 and may not include a microclimate fabric layer 212, or at least is not shown in FIG. 2E. The weight support system 250 includes a 3-layer foam stack up 252 and a floating top layer 254 to reduce shear. The top layer 254 may be floating in a sense that it is not entirely securely attached to the rest of the layers. The top layer 254 may be an open-cell polyurethane foam 256 to prevent overheating characteristics of other memory foams. The weight support system 250 may also include teardrop foam structures 258 in the second layer of foam in the sacrum and heel zones for improved passive pressure relief. The weight support system 250 may further include a heel zone slope for increased comfort. At both side edges, the weight support system 262 may include support walls 262 to aid entry and exit. The weight support system 262 may further include articulation cuts 264 at pivot points in the bottom layers. The articulation cuts 264 reduces the image artifacts of the sensor grid layer 214.

Example Sensor Grid Configuration

Figure 3A:
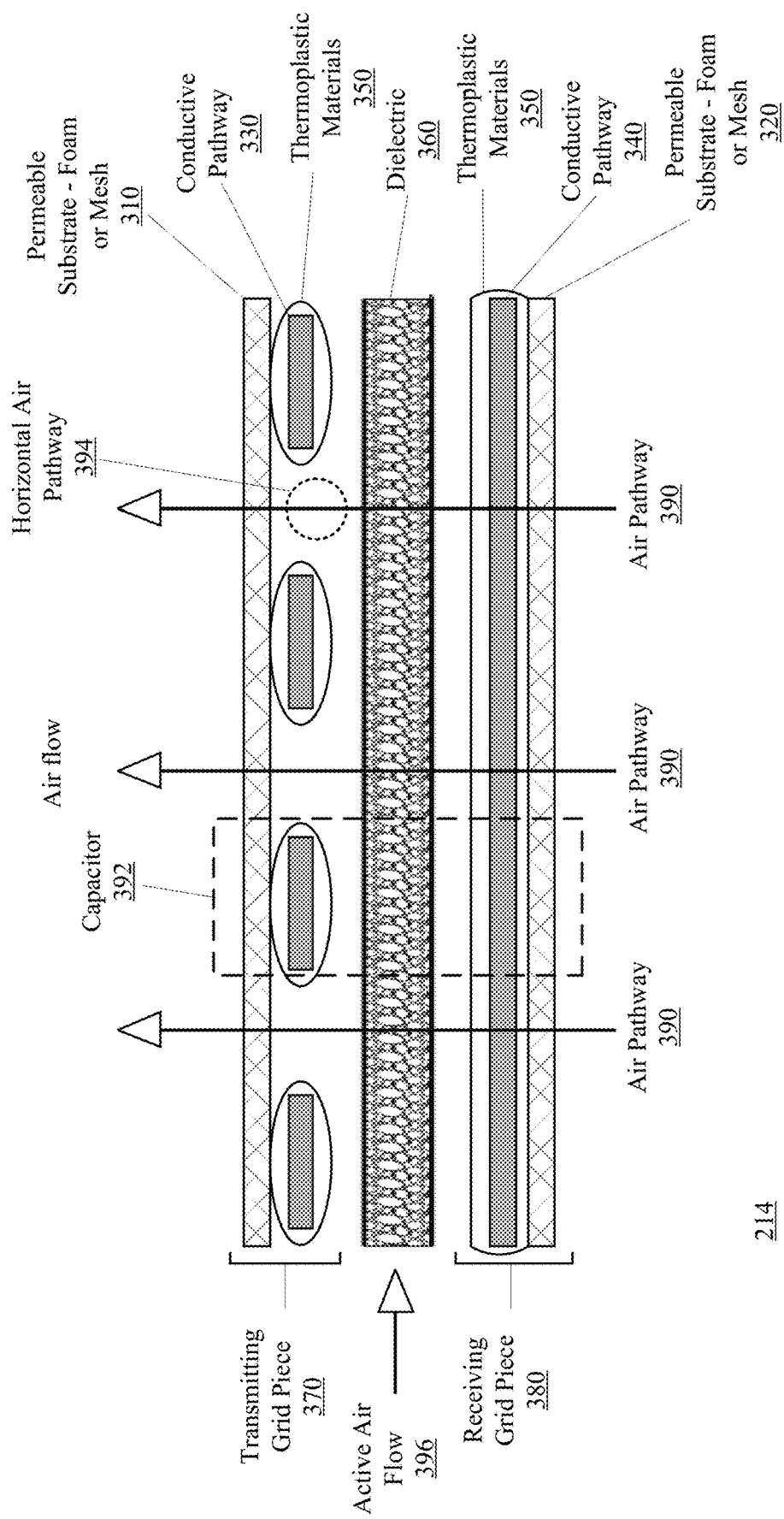
FIG. 3A is a conceptual diagram illustrating a cross-sectional view of an example sensor grid layer, in accordance with some embodiments, in accordance with some embodiments.
Figure 3B:
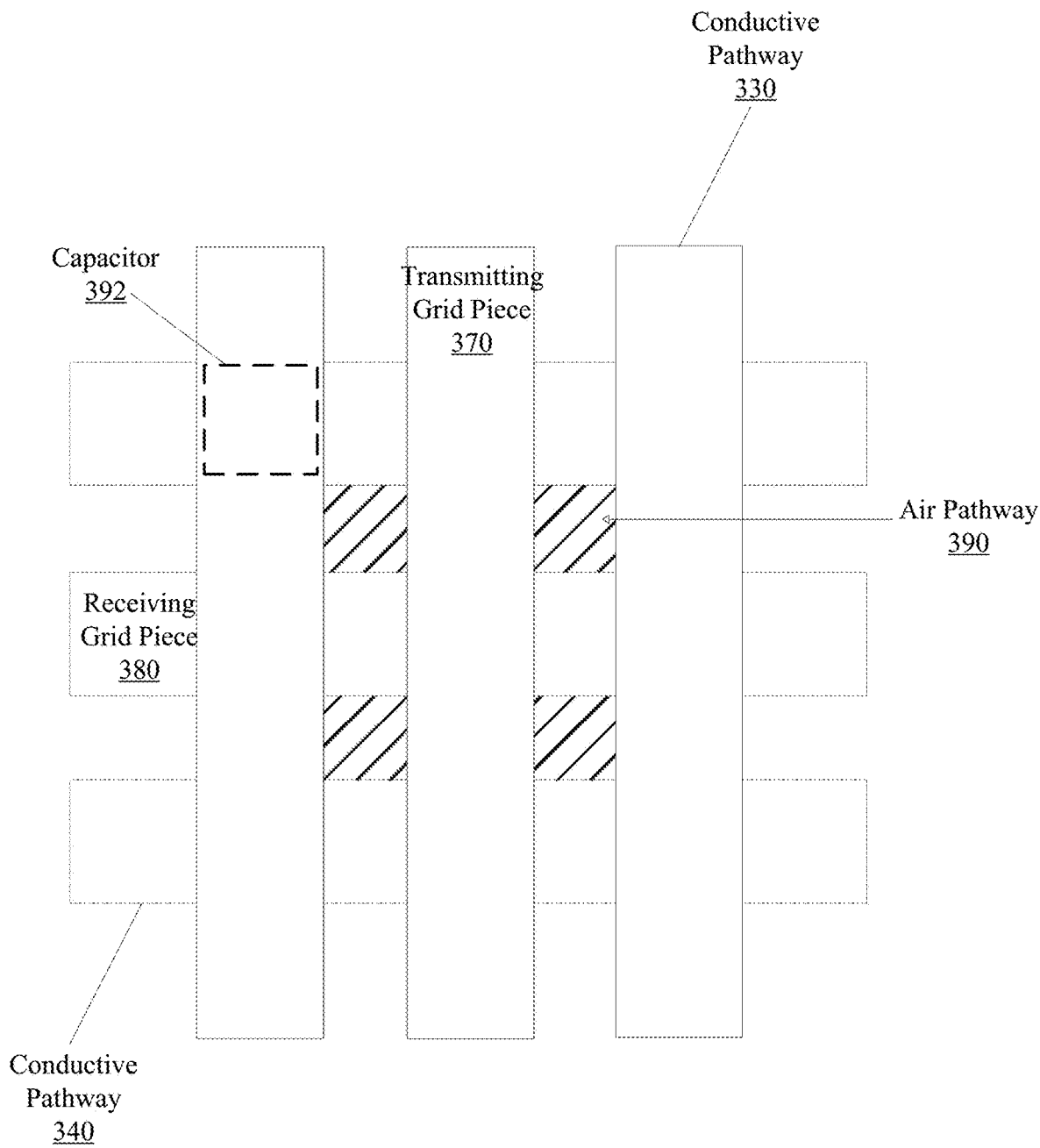
FIG. 3B is a conceptual diagram illustrating the top view of the sensor grid layer shown in FIG. 3A.

FIG. 3A is a conceptual diagram illustrating a cross-sectional view of an example sensor grid layer 214, in accordance with some embodiments. FIG. 3B is a conceptual diagram illustrating the top view of the sensor grid layer 214. The example configuration shown in FIGS. 3A and 3B is an air-permeable sensor grid layer 214 that promotes the airflow of an entire weight support system 110. Conventionally, capacitive grid sensors are produced by bonding conductive strips to a continuous elastomer, which serves as the physical substrate holding the conductive strips in place. This elastomer is non-permeable by design. When this style of the grid is combined with a dielectric material to form a capacitive pressure sensor, the impermeable elastomer substrate is present throughout the entire sensor grip area, rendering the sensor grid layer impermeable.

Referring to FIG. 3A, the air-permeable capacitive sensor grid layer 214 includes a first permeable substrate 310, a second permeable substrate 320, a first set of electrically conductive pathways 330, a second set of electrically conductive pathways 340, thermoplastic materials 350, and a dielectric layer 360. The first set of electrically conductive pathways 330 bonded to the first permeable substrate 310 may serve as the transmitting grid piece 370 that transmits electrical signals and the second set of the electrically conductive pathways 340 bonded to the second permeable substrate 320 may serve as the receiving grid piece 380 where attenuated electrical signals are detected. The transmitting grid piece 370 and the receiving grid piece 380 may be identical or substantially similar, except the receiving grid piece 380 is flipped and rotated 90 degrees so that the first set of electrically conductive pathways 330 are arranged in the longitudinal direction and the second set of electrically conductive pathways 340 are arranged in the lateral direction. The sublayers shown in FIG. 3A of the sensor grid layer 214 may simply be referred to as layers.

The first permeable substrate 310 and a second permeable substrate 320 may be formed from air permeable materials such as foam or meshes, or any materials or fabrics that largely do not obstruct airflow through the substrates. An example material may be an open-cell compressible thermoplastic polyurethane (TPU) elastomer. The first permeable substrate 310 and a second permeable substrate 320 may allow free airflow to basically the entire surface area of the substrates. The first permeable substrate 310 and a second permeable substrate 320 each carries a plurality of electrically conductive pathways and the conductive pathways may be securely coupled (e.g., bonded) to the substrate. In some embodiments, the substrates securely position the electrically conductive pathways to define the sensor grid. In addition, the substrates may also securely position the electrically conductive pathways that are impermeable to air to be spaced apart to define a plurality of air pathways 390 to create an air-permeable capacitive sensor grid. In one embodiment, the first permeable substrate 310 and a second permeable substrate 320 may have a moisture vapor transmission rate of at least 270 g/m$^2$/24 h. In one embodiment, the first permeable substrate 310 and a second permeable substrate 320 may have a moisture vapor transmission rate of 1300 g/m$^2$/24 h. Air permeability may be tested under ASTM E96—Standard Test Methods for Water Vapor Transmission of Materials.

The first set of electrically conductive pathways 330 and the second set of electrically conductive pathways 340 are formed from conductive materials such as metallic conductive strips or wires. Owing to the materials used, the electrically conductive pathways may be air impermeable. For example, the electrically conductive pathways may be individually encapsulated or otherwise covered by a thermoplastic material 350 that insulates the electrically conductive pathways. The thermoplastic material 350 may also be air impermeable. The first set of electrically conductive pathways 330 may be arranged in a first orientation and the second set of electrically conductive pathways may be arranged in a second orientation that is different from the first orientation. The first and second sets of electrically conductive pathways cross over each other to form intersections that have a dielectric layer 360 sandwiched between the two conductive pathways, thereby forming a capacitor 392 at each intersection. Each capacitor 394 is a sensing point of the sensor grid layer 214 and the network of intersections form a matrix of sensing points that can generate different measures of capacitance across different areas of the weight support system 110. The capacitance may be proportional to or other correlated with the force and pressure exerted on the area as the pressure compresses the area of the sensor grid layer 214 and reduces the distances between the top conductive pathway and the bottom conductive pathway.

The arrangement of the electrically conductive pathways that are in longitudinal and lateral directions shown in FIG. 3B is only an example configuration. In various embodiments, the first set of electrically conductive pathways 330 and the second set of electrically conductive pathways 340 may be arranged relative to each other in any suitable manners and directions, perpendicular or not, regularly or not, symmetrical or not. The electrically conductive pathways in each set may also be arranged in a manner that is different from the configuration shown in FIG. 3B, whether the electrically conductive pathways are straight or curved, branched or unbranched, evenly spaced or not, aligned parallelly or not, and with same orientation or not. For example, instead of having evenly distributed electrically conductive pathways so that the weight support system 110 has roughly the same number of sensing points in various areas, in some embodiments the electrically conductive pathways may be spaced more densely in certain target areas so that the target areas have a higher number of sensing points compared to other peripheral areas.

Each electrically conductive pathway in the first set 330 and the second set 340 may be spaced apart from the neighboring electrically conductive pathways to create horizontal air pathways 394. The horizontal air pathways created by the first set of electrically conductive pathways 330 and the horizontal air pathways created by the second set of electrically conductive pathways 340 may be oriented differently due to the different orientations of the electrically conductive pathways in the first and second set. The intersections of the horizontal air pathways form vertical air pathways 390. In some embodiments, the vertical air pathways 390 may contain only the permeable substrates 310 and 320 and the permeable dielectric layer 360. In some embodiments, in order to further promote the airflow in the vertical air pathways 390, the dielectric layer 360 may be cut out at the vertical air pathways 390. In some embodiment, to even further promote the airflow, the permeable substrates 310 and 320 may also be cut out at the vertical air pathways 390.

Each electrically conductive pathway may be individually encapsulated by a thermoplastic material 350. The thermoplastic material 350 may be formed from flexible, insulating, and dielectric materials that are preferably as thin as possible. For example, in some embodiment, the thermoplastic material 350 may be an elastomer such as urethane. Other thermoplastic elastomers (TPE) or thermoplastic polyurethanes (TPU) may also be possible. The thermoplastic material 350 provides insulation and protection to each electrically conductive pathway to prevent short circuit or cross talk of the conductive pathways. The thermoplastic material 350 also surrounds the conductive pathway and serves as a bonding medium to secure the conductive pathway to the permeable substrate 310 or 320. While other insulating materials may be used, the thermoplastic material 350 is used in the example shown in FIG. 3A so that the thermoplastic material 350 can be heat activated to be heat laminated and thermally bonded to the permeable substrate 310 or 320. In some embodiments, each electrically conductive pathway is individually encapsulated so that the encapsulated electrically conductive pathway can be spaced apart and form horizontal air pathways to promote the air permeability of the sensor grid layer 214.

The dielectric layer 360 is sandwiched between the transmitting grid piece 370 and the receiving grid piece 380. The dielectric layer 360 may be formed of a permeable material such as polyurethane foam so that air can pass through the layers of the weight support system 110. In some embodiments, both the dielectric layer 360 and the permeable substrates 310 and 320 may use the same types of materials, such as open-cell polyurethane foam.

An air-permeable sensor grid offers various advantages over conventional urethane laminated sensor grid. For example, an air-permeable sensor produces significantly less noise generated when layers around the sensor rub against the air-permeable grid. An air-permeable sensor grid also increases user comfort due to airflow through permeable grid layers. An air-permeable sensor grid also decreases heat retention from the reduction in urethane and increased permeability in the sensing layer. An air-permeable sensor grid further simplifies surface temperature and humidity monitoring. An air-permeable sensor grid also allows an integration of active cooling technologies for moisture and surface temperature control such as low air loss mattresses. For example, an active airflow source 396 (e.g., generated from the airflow system 120 in FIG. 1) may direct air into inner layers of the sensor grid.

Example Sensor Grid Production Process

Figure 4A:
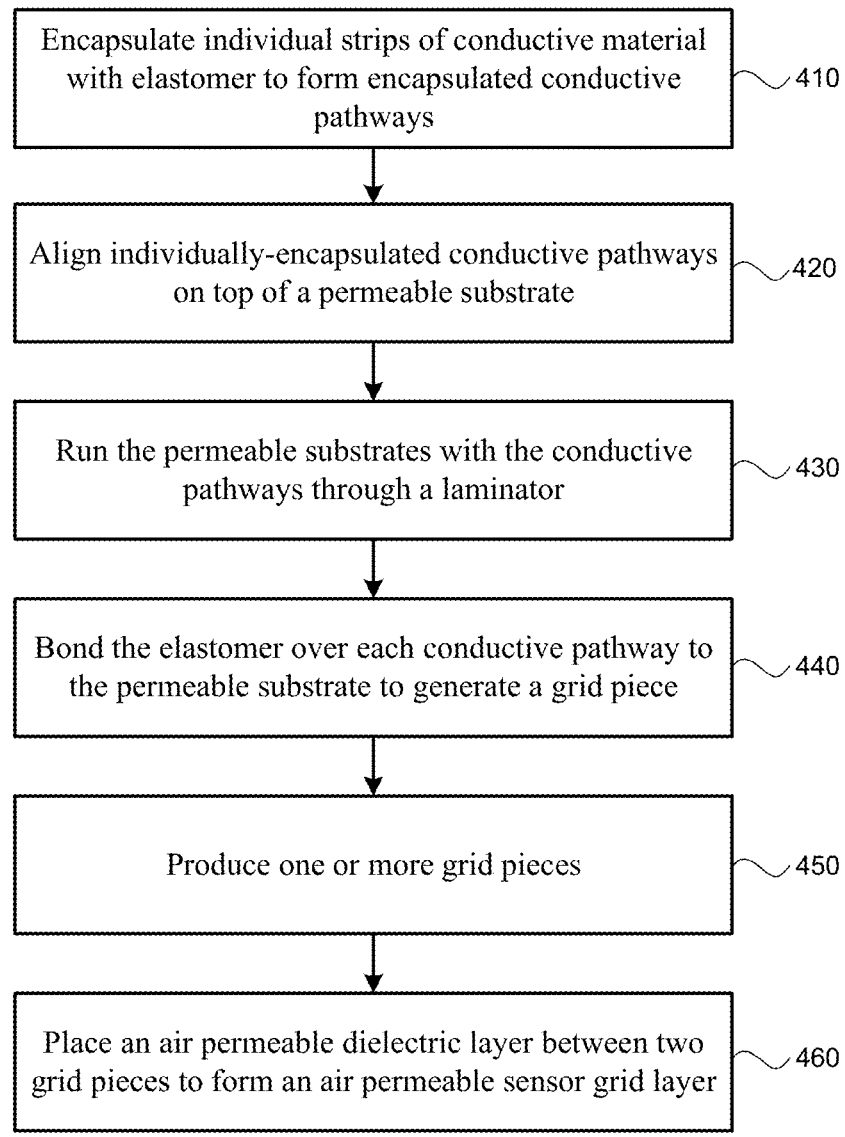
FIG. 4A is a flowchart depicting an example process for producing an air-permeable sensor grid layer, in accordance with some embodiments.
Figure 4B:
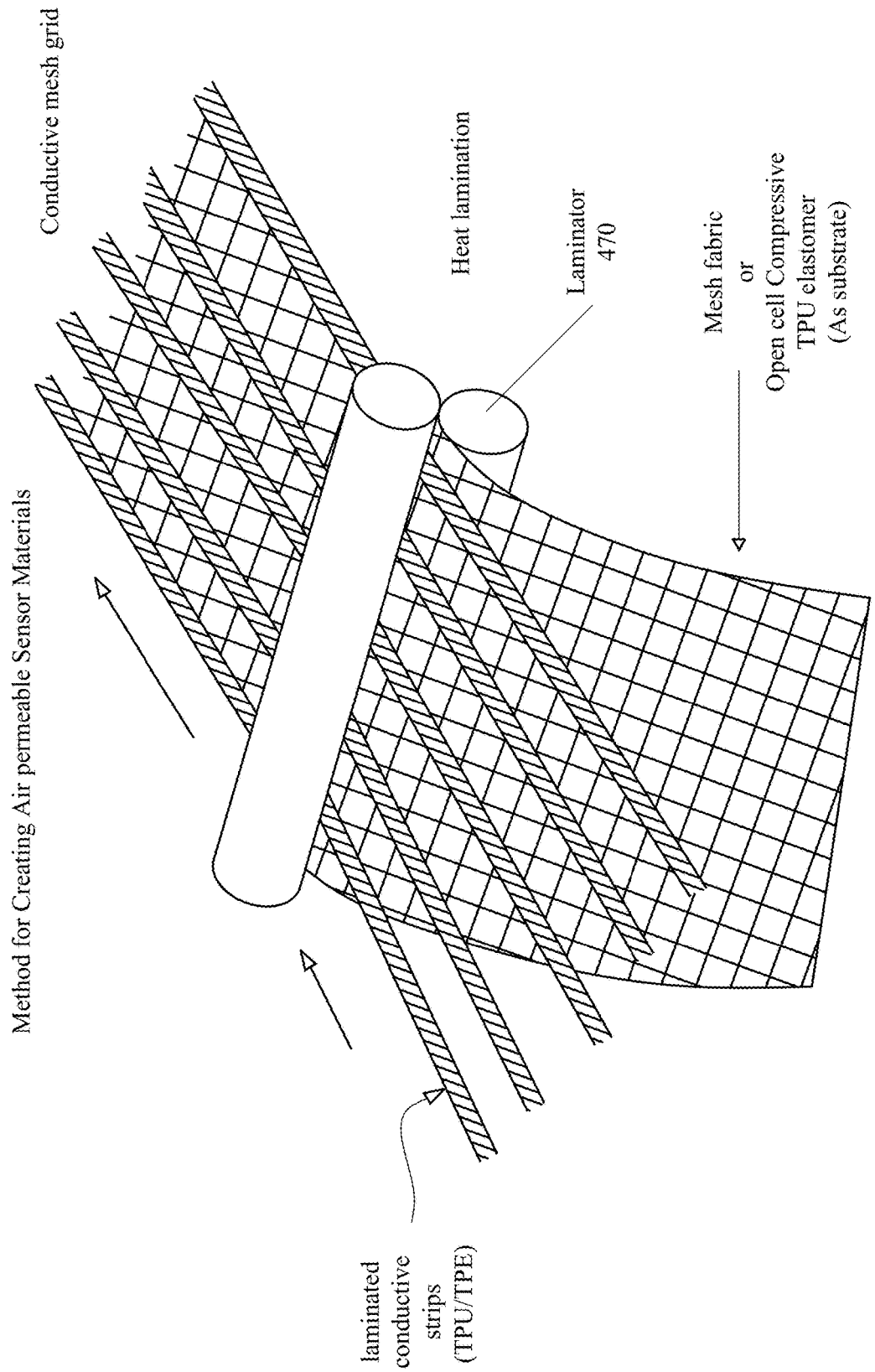
FIG. 4B illustrates an example lamination process, in accordance with some embodiments.

FIG. 4A is a flowchart depicting an example process 400 for producing an air-permeable sensor grid layer 214, in accordance with some embodiments. During the production process 400, individual strips of conductive material may be encapsulated 410 with a thermoplastic elastomer such as urethane) to form encapsulated conductive pathways. The elastomer serves to physically and electrically isolate each conductive strip to form an individual conductive pathway. By individually encapsulating the conductive pathways in the elastomer, each conductive pathway is not physically connected to its neighboring conductive pathways with continuous elastomer. A series of individually-encapsulated conductive pathways may be aligned 420 on top of a permeable substrate material (e.g., foam or mesh). The permeable substrate 310 or 320 with the conductive pathways may run 430 through a laminator 470. FIG. 4B illustrates an example lamination process, in accordance with some embodiments. The elastomer over each conductive pathway is bonded 440 to the permeable substrate 310 or 320 to generate a grid piece 370 or 380 where the strips are held in alignment (e.g., parallel alignment) and the gaps between strips allow airflow. The conductive pathways with the elastomer may be thermally bonded to the permeable substrate 310 or 320. Alternative bonding methods such as adhesive and pressure bonding may also be used. Two of such grid pieces 370 and 380 may be produced 450 using the same or similar method. One of the grid pieces may be flipped and turned 90 degrees. An air-permeable dielectric layer may be placed 460 between the two grid pieces to form an air permeable sensor grid layer 214.

Permeable sensors built with the process 400 have the benefit of being more flexible than their traditional counterparts, as well as being much quieter during use. Traditional sensors must also be built with air handling in mind. To prevent air from becoming trapped between conductive grid layers and impacting capacitance, physical routes of airflow must be built into the sensor. Permeable sensors avoid this problem entirely as air can flow freely through all layers of the sensor. Also, the process 400 simplifies the production process. The permeable substrate 310 or 320 provides a platform to secure individual conductive pathways that need to be spaced apart to generate air pathways. The encapsulation of the conductive pathways provides a way to bond the metallic pathway to the air-permeable substrate.

Example Signal Processing

Figure 5A:
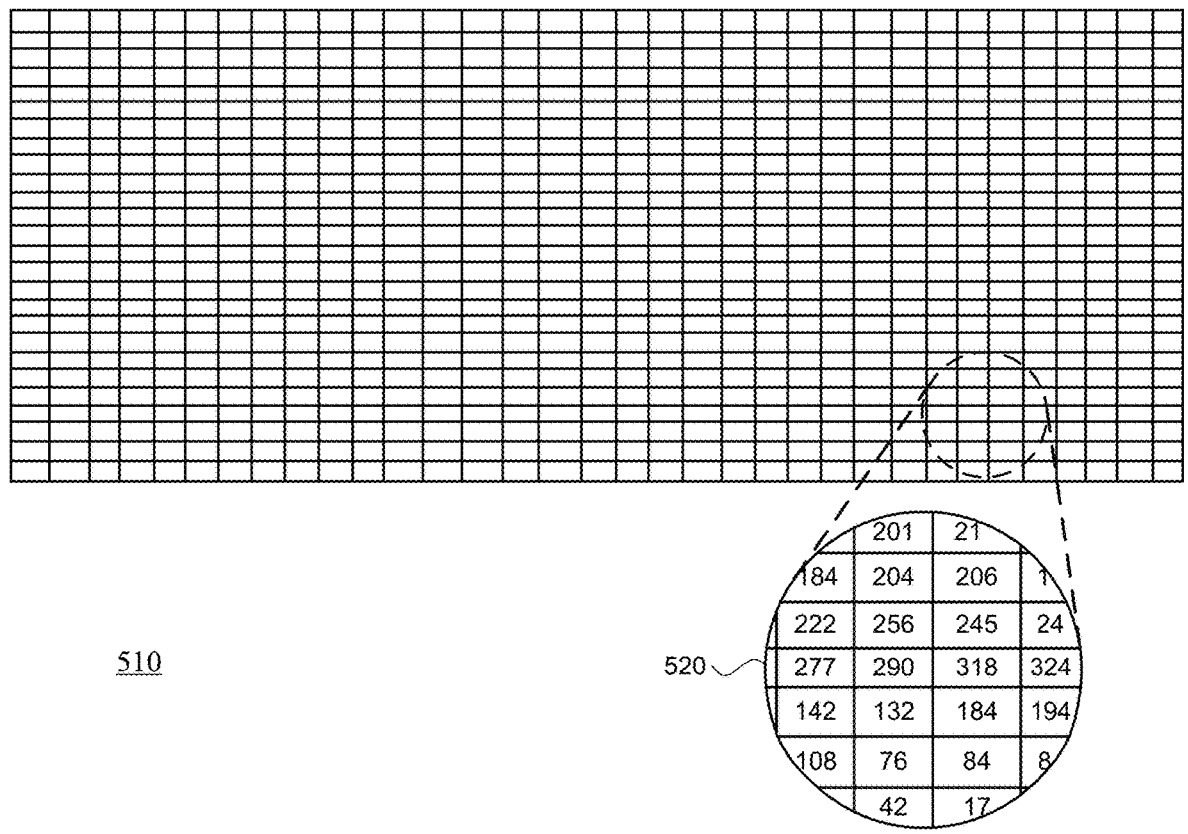
FIG. 5A is a conceptual diagram of a matrix of sensor readings generated by a sensor grid layer, in accordance with some embodiments.

FIG. 5A is a conceptual diagram of a matrix 510 of sensor readings generated by a sensor grid layer 214, in accordance with some embodiments. The sensor grid layer 214 includes a plurality of sensing points. Each of the sensing points can generate a sensor reading such as a pressure reading. The signals from the sensor grid layer 214 may generate a matrix 510 of sensor readings. The inset 520, which shows an enlarged area of the matrix 510, illustrates that each grid position that corresponds to a sensing point provides an individual sensor reading value.

Figure 5B:
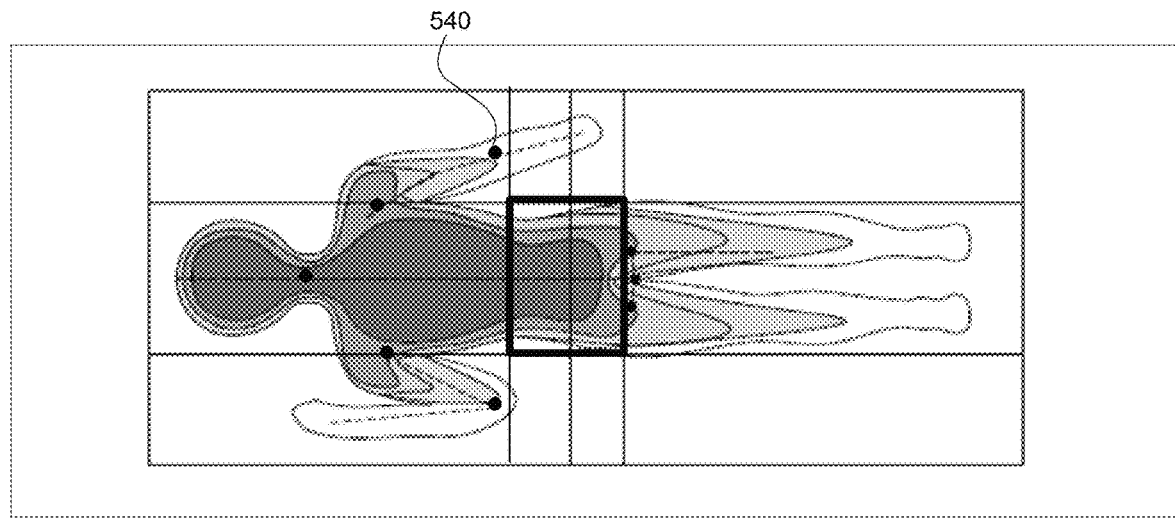
FIG. 5B is a conceptual diagram illustrating an example pressure heatmap that is generated by a matrix of sensor readings, in accordance with some embodiments.

FIG. 5B is a conceptual diagram illustrating an example pressure heatmap 530 that is generated by the matrix 510 of sensor readings, in accordance with some embodiments. The values of the sensor readings may be converted to various colors or greyscales to illustrate the pressure distribution on the weight support system 110. For example, the pressure heatmap 530 shows a greyscale heatmap in which higher pressure values are associated with darker colors. Because the area of the weight support system 110 without the person should detect significantly less pressure than the area on which the person is sleeping, the area without the person is shown as white. An outline of the person may be detected based on the sensor readings. When the person moves, the sensor grid layer 214 generates different sensor readings. The heatmap 530 and the outline of the person are also changed as a result. In some embodiment, the heatmap 530 may also be in a color scheme. For example, low-pressure areas will be shown using cooler colors and high-pressure areas will be shown using warmer colors.

A computer (e.g., the computing server 140, the local computer 130, and the user device 170) may process the data from the sensor grid layer 214 and generate different results related to the person. The computer may use one or more machine learning models and other data processing techniques to deduce positions of various joints 540 of the person, the outline of the person, and the pose of the person. The identified joint positions may be expressed in two-dimensional coordinates or three-dimensional coordinates that take account of the height of various body positions. The machine learning techniques will be further discussed in FIG. 6A through FIG. 9. The computer may also identify certain target body parts of the person, such as the lumbar region as shown in the heatmap 530.

Data generated from the weight support system 110 allows a computer to intelligently identify selected areas of the body and extract bio-signals from certain target areas. Both the body and joint positions may be used to identify regions on the body which are then monitored to detect physiological signals. This identification procedure significantly reduces signal noise and allows for more accurate monitoring. For example, the rectangle shown in the heatmap 530 demonstrates how a region of the body can be selected (lumbar) using the joint detection system (convolutional neural network with pre and post processing). This region can then be used to identify a bio-signal associated with the area of the body. For example, the respiration rate may be identified by locating the lumbar section of the body. Another example is temperature monitoring. The user's body outline can be identified using the pressure sensor. The thermistors located in contact with the user can be used to monitor skin temperature.

Figure 5C:
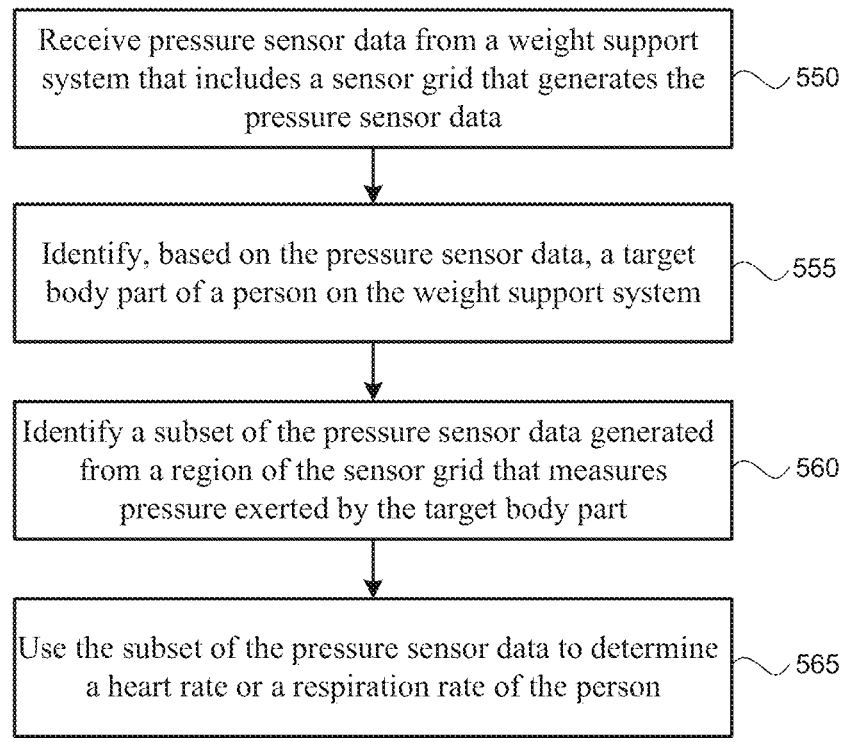
FIG. 5C is a flowchart depicting an example process for determining respiration rates or heart rates of a person using data from a sensor grid layer, in accordance with some embodiments.

FIG. 5C is a flowchart depicting an example process for determining respiration rates or heart rates of a person using data from the sensor grid layer 214, in accordance with some embodiments. A computer receives 550 pressure sensor data from a weight support system 110 that includes a sensor grid that generates the pressure sensor data. The weight support system 110 may be a bedding system or a seating system. The pressure sensor data may be in a particular format, such as in the matrix format 510 shown in FIG. 5A. The pressure sensor data may be a two-dimensional dataset that has different reading values that correspond to the pressure readings of various areas of the weight support system 110.

The computer identifies 555 a target body part of the person on the weight support system 110. The identification of the target body part may be based on the pressure data. As shown in FIG. 5B, based on the pressure data, a heatmap 530, the outline of the body, and various joint positions may be identified. The pressure sensor data may be in the format of a time series of matrix 510. For example, the sensor grid layer 214 may capture readings at a certain frequency. Since the person, who may be sleeping on the weight support system 110, may move, the pressure readings in the matrix 510 over time may also change. For a particular instance in time, the computer may generate the outline of the body based on the pressure readings in the matrix 510 at the particular instance. The computer may use one or more machine learning techniques such as a convolutional neural network (CNN) to identify the joint positions of the persons by inputting the matrix 510 of pressure data at the particular instance in time to the CNN. For the time series, the computer may repeat the process and identify the joint positions and outline of the person in the time series. For a particular instance in time, based on the joint positions, the computer may identify the target body part such as a lumbar region as shown in FIG. 5B.

The computer identifies 560 a subset of the pressure sensor data generated from a region of the sensor grid layer 214 that measures the pressure exerted by the target body part. For example, in the lumbar region shown in FIG. 5B, the pressure sensor data from the region enclosed by the rectangle may be used. Since the pressure sensor data may be a time series that keeps track of changes in pressures and movements of the person, the region of the sensor grid layer 214 that corresponds to the target body part can change from time to time. Based on the time series of pressure sensor data, the computer keeps track of the region and extract pressure sensor data from the region.

The computer uses 565 the subset of pressure sensor data to determine a heart rate or a respiration rate of the person. For example, the computer may calculate a spatial average pressure corresponding to the region based on the subset of the pressure sensor data generated from the region. The spatial average may be a simple average or a weighted average. Each spatial average may correspond to a particular instance in time. The computer may generate a time series of pressure readings corresponding to the region. The computer, based on the time series of averaged pressure readings in the region, may determine the heart rate or the respiration rate of the person. The time series may show a certain cycle of pressure changes in the region. The cycle may correspond to the target rate to be measured. The cycle may also be associated with a range of amplitudes. Various digital signal processing techniques may be used in determining the target rate.

By way of example, the respiration rate may be a key vital sign for continuous monitoring in health care applications. Adults typically have a respiration rate of 12-20 breaths per minute (BPM). Changes in this signal in terms of amplitude, frequency, and the variation in time duration between breaths can be used to identify useful clinical information such as coughing, hyperpnea, and respiratory failure risk. Conventional methods of monitoring respiration rate can range from a wired photoplethysmography (PPG) sensor to strain-gauge-based respiration belts, both of which may have detrimental effects on the user's comfort.

The intelligent weight support system 110 can monitor the respiration rate without such connections, though information from other sensors besides the pressure sensor may be used to provide richer information to the respiration rate detection algorithm. After identifying the target body part using the joint detection algorithm, the computer calculates the average pressure of that area. This is placed in series with previously calculated values to create a time series signal. This time series may approximately represent the thoracic pressure generated by the person's breathing.

A sliding window takes a segment of that time series of thoracic pressure and passes that through a filter to determine the user's respiration rate. According to some embodiments, the computer may use a Finite Impulse Response (FIR) filter using a Kaiser window to identify the respiration rate within the desired bandwidth. The signal captured by the respiration rate detection algorithm may approximate the thoracic pressure instead of being just a discrete respiration rate. The extracted time series signal may be further manipulated to extract other meaningful features and statistics such as breath rate variability BRV.

With respect to determining the heart rate, the heart rate is another key vital sign for continuous monitoring in health care applications and other applications. Normal adult heart rates range from 60 to 100 beats per minute (BPM). Like the respiration rate, changes in this signal in terms of amplitude, frequency, and the variation in time duration between heartbeats can be used to identify useful clinical information such as arrhythmia or risk of myocardial infarction. Conventional methods of monitoring heart rate can range from the use of an electrocardiogram (ECG), which requires electrodes to be connected to multiple spots on a patient's body, to the use of a wired PPG sensor, both of which may have detrimental effects on the user's comfort.

Like with respiration rate, the intelligent weight support system 110 can monitor without such wired connections, though the use of additional sensors to provide richer information to the system is also possible. The two-dimensional coordinates for joints and other sensor information are combined to identify a target body part such as the chest area. A sliding window takes a segment of that time series signal and passes it through a filter to determine the user's heart rate. An FIR filter in conjunction with other signal processing techniques can be used to identify heart rate.

Another feature that can be useful in clinical situations is movement. Monitoring patient broad and micro-movements can allow for the detection of seizures, talking, eating, drinking, falls and fall probability. This feature is also extremely useful for detecting patient motion that may interfere with the recording of other bio-signals (a sudden movement may impact recorded heart rate or respiration rate). The intelligent weight support system 110 can detect movement through both rapid changes in the system pressure readings and through the position and joint detection models.

The pressure frame can be processed in multiple ways to extract meaningful movement analysis features. For example, the average pressure of the frame may be calculated and placed in a time series with the past frame's average pressure to generate a signal. The time series may be created using each frame's average pressure. Raw frames may be fed into a CNN to extract useful features such as body movements tied to specific body parts.

Example Sleep State Detection Processes

Figure 6A:
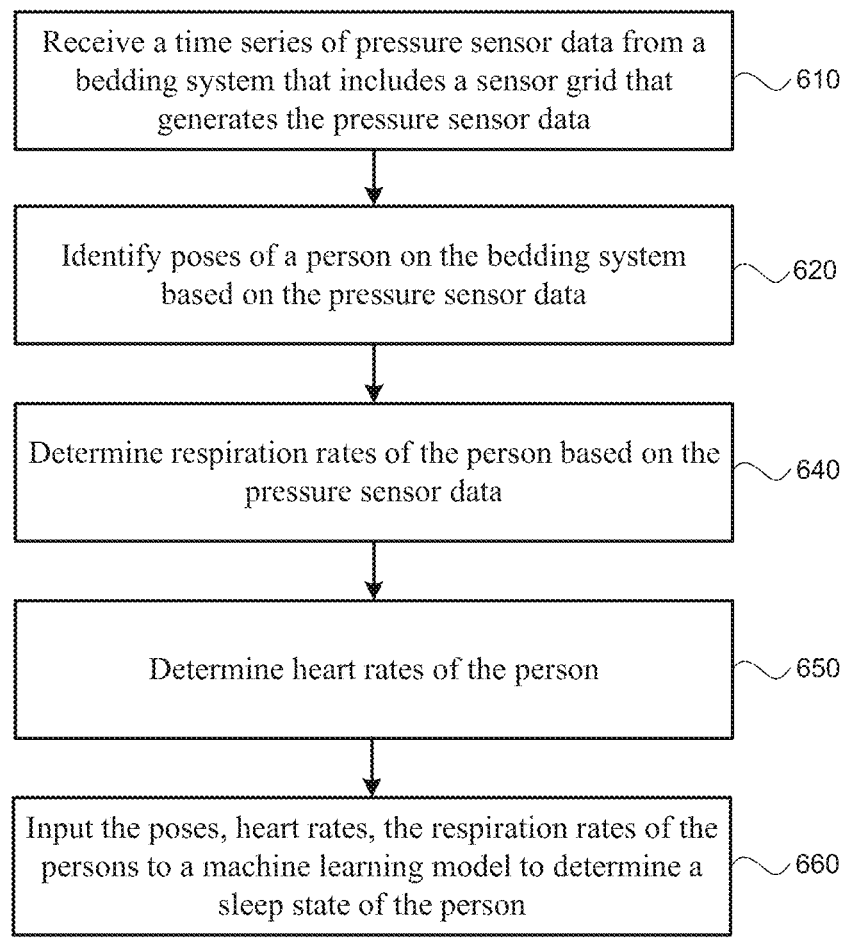
FIG. 6A is a flowchart depicting an example process for determining the sleep state of a person using the sensor data generated by a weight support system, in accordance with some embodiments.
Figure 6B:
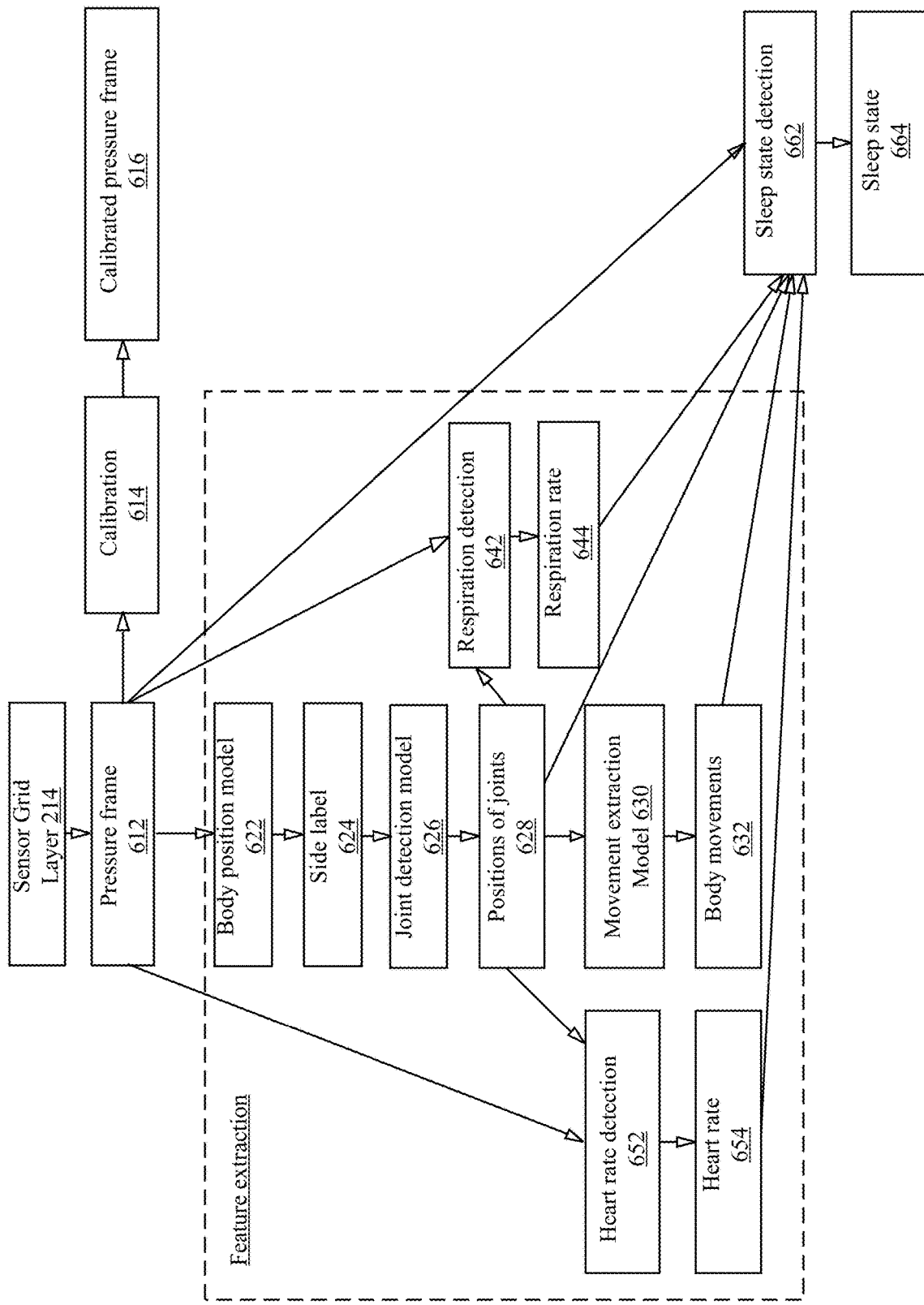
FIG. 6B is a block diagram illustrating an example algorithmic pipeline for sleep state detection, in accordance with some embodiments.

FIG. 6A is a flowchart depicting an example process 600 for determining the sleep state of a person using the sensor data generated by the weight support system 110, in accordance with some embodiments. A computer, which may be the computing server 140, the local computer 130, or the user device 170, may perform the process 600. FIG. 6B is a block diagram illustrating an example algorithmic pipeline that includes different stages and outputs that are used to process the sensor data generated by the weight support system 110 to determine various sleep states of the person. FIG. 6A is discussed in conjunction with FIG. 6B.

The computer receives 610 a time series of pressure sensor data from a weight support system 110. The weight support system 110 includes a sensor grid layer 214 that generates the pressure sensor data. The weight support system 110 may be a bedding system. The time series of pressure sensor data may be the raw pressure frame data 602. The raw pressure frame data 602 may include a time series of matrix readings similar to the matrix 510. In some cases, the sensor grid layer 214 may need a calibration process 614 that generates the calibrated pressure frame 616.

Figure 6C:
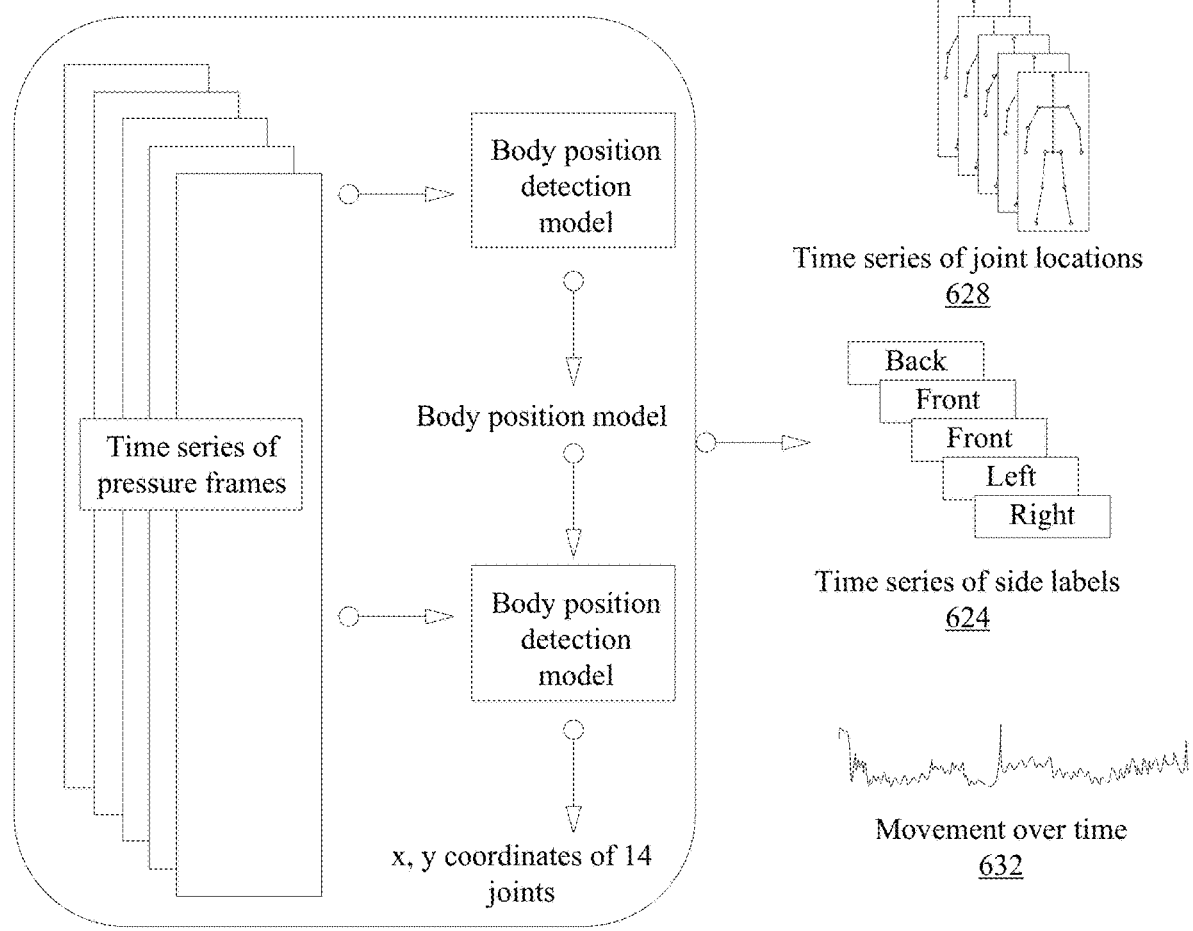
FIG. 6C is a conceptual diagram showing the pipeline of generating various data related to a person's poses, in accordance with some embodiments.

The computer identifies 620 poses of a person on the bedding system based on the pressure sensor data. FIG. 6C is a conceptual diagram showing the pipeline of generating various data related to the position of the person, in accordance with some embodiments. The computer may use the time series of pressure sensor data to perform various analyses related to the person's poses. The pose of the person may include some or all of the joint location data, side labels, and/or movement over time.

For example, the computer may use a body position model 622, which may be a machine learning model that generates the side label 624 of the person given a particular instance in time. The computer may input the pressure sensor data to the body position model 622 to determine the side label 624. The side label 624 may determine whether a person is sleeping on the left side, on the right side, on the front side, or on the backside. In one embodiment, the side label 624 may include prone, supine, left side, right side, sitting, and sitting on the edge.

The computer may use a joint detection model 626. The joint detection model 626 may be a CNN that receives pressure sensor data and identify the outline and certain target joints of the persons. Depending on the model, there can be a predetermined number of target joints (such as 14). The target joints allow the computer to model the pose of the person similar to a stick figure. The pose model helps the joint tracking model to track the body. The CNN may output the positions of joints 628 as two-dimensional coordinates (or three-dimensional coordinates) and a the confidence probability between 0 and 1 for each joint position. The computer may then generate a skeleton of the user and determine the 2D spatial coordinates for 14 joints along with their probability. The example 14 joints may be hip, effector head, right shoulder, right forearm, right hand, left shoulder, left forearm, left hand, right thigh, right shin, right foot, left thigh, left shin, and left foot.

The computer may use a movement extraction model 630 to generate the body movements 632 of the person. Movement over time can be decomposed into the movement of specific body parts or joints over time given the information provided by the CNN. The body movements 632 may detect the magnitudes of the movement of the person over time.

In various embodiments, the body position model 622, the joint detection model 626, and the movement extraction model 630 may be determined using the same model or separate models. For example, in one embodiment, a CNN can be trained to generate positions of joints 628, body position labels such as side labels 624, and body movements 632 over time together using the time series of pressure sensor data. To determine the poses of the person, the computer may arrange, for a particular instance in time, the pressure sensor data as a matrix of pressure readings. The computer may input the matrix of pressure readings to a CNN for a particular pose at the particular instance. The computer may generate other poses in other instances in time using the CNN. In some embodiments, the body position model 622, the joint detection model 626, and the movement extraction model 630 may be separate machine learning models that are specialized in generating certain types of pose data. For example, the body position label and the pressure frame 612 is passed to one of multiple trained CNN machine vision processes based on what body position classification is identified. The CNNs are trained on a combination of 2D matrices of pressure values and 3D motion-captured body data to generate the positions of joints 628.

The computer also determines 640 respiration rates of the person based on the pressure sensor data. The detection 642 of the respiration rate 644 may include receiving the pressure sensor data 612 in time series and the position of joints 628 to identify a target body part. Both the body and joint positions may be used to identify regions on the body which are then monitored to detect physiological signals. This identification procedure significantly reduces signal noise and allows for more accurate monitoring. The rectangle 540 shown in the heatmap 530 demonstrates how a region of the body can be selected (lumbar) using joint detection. This region can then be used exclusively to identify a bio-signal associated with that area of the body. Using the target body part, the computer may determine a subset of pressure sensor data 612 that is used to determine the respiration rate 644. An example process 500 used to determine the respiration rate is discussed in FIG. 5C. Other ways, such as using an external vital sensor 115, may also be used to determine the respiration rates.

Figure 6D:
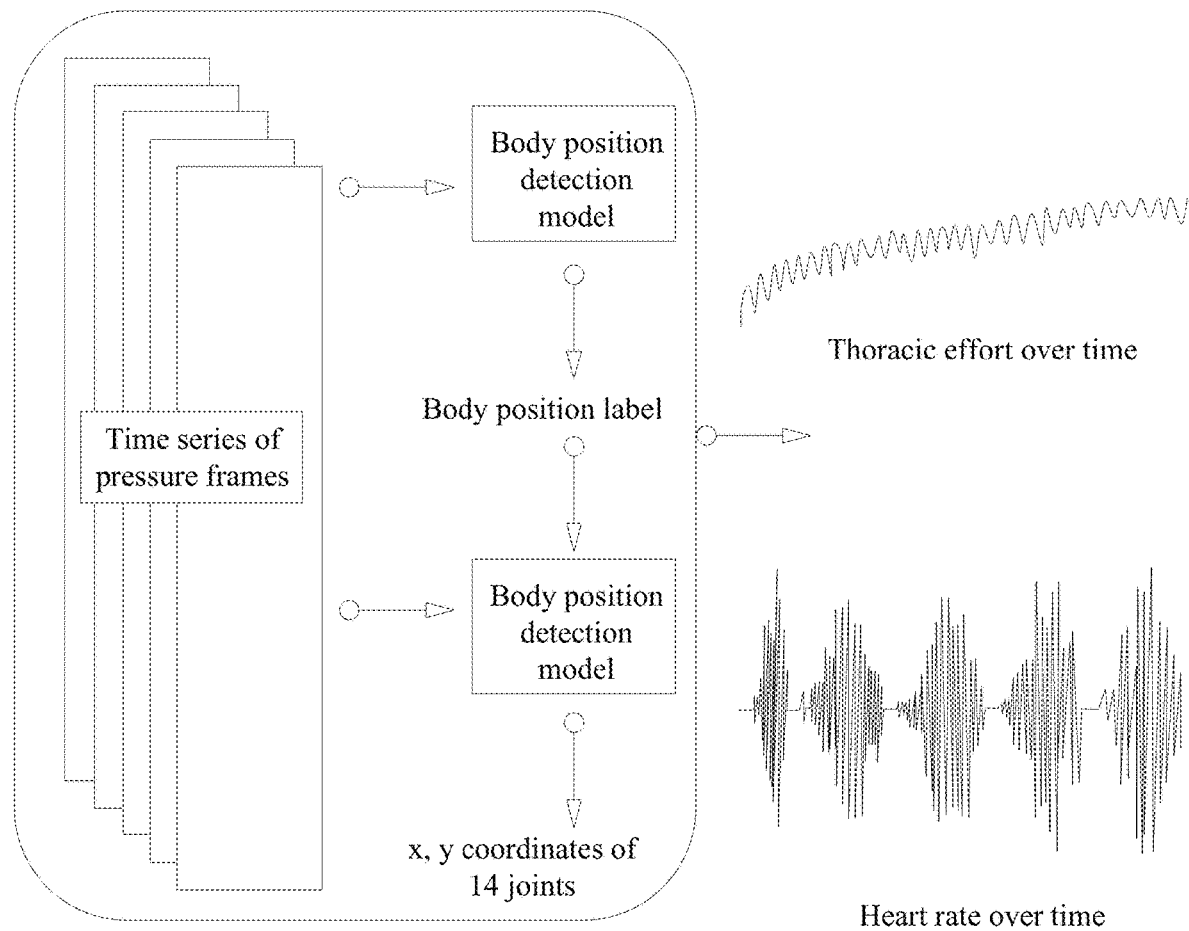
FIG. 6D is a conceptual diagram illustrating the generation of respiration rates and heart rates, in accordance with some embodiments.

The computer may also determine 650 the heart rates 654 of the person using a heart rate detection process 652. In various embodiments, the heart rate may be detected in different ways. In some embodiments, the heart rate detection process 652 may rely on the pressure sensor data 612 and the positions of joints 628 to determine the heart rates using the process 500. In other embodiments, the heart rate may be detected using the sensor data generated by the piezoelectric sensor 226 shown in FIGS. 2B and 2D. In yet other embodiments, the heart rate may be detected using an external vital sensor 115, such as a smartwatch worn by the person or a medical graded heart rate monitor device used in the hospital setting. FIG. 6D is a conceptual diagram illustrating the generation of respiration rates and heart rates. Respiration and heart rates may be extracted from the pressure data, as discussed in FIG. 5C.

The computer inputs 660 the poses, heart rates, and the respiration rates of the person to another machine learning model to determine a sleep state 646 of the person at a sleep state detection stage 662. In various embodiments, one or more types of input data may be omitted. For example, in some embodiments, only the respiration rates and the poses are needed to input to the machine learning model. The features extracted from the poses, heart rates, and the respiration rates of the person can be fed into one or more machine learning models to automatically determine if the user is awake, or in one of the following sleep states: N1, N2, N3, or REM sleep. The sleep state is one of candidate sleep states. For the purpose of determination, the awake state may be treated by the machine learning model also as one of the candidate sleep states. The machine learning model generates a probability that the person is in a particular candidate sleep state for each candidate state. The sleep state selected as the output may be the particular candidate sleep state with the highest probability.

The feature extracted that may be used as the input of the machine learning model in the sleep state detection 662 may include one or more of the following. For example, the features may include pressure features, such as average pressure over time or peak pressure over time. The feature may also include pressure on the body features, such as pressure on a joint or body section over time. The features may also include vital sign features, such as respiration or heart rates over time. Other features, such as other vital sign features that are not explicitly mentioned, may also be part of the input to the machine learning model.

Given these features, time-series analysis machine learning models such as Long-Short Term Memory (LSTM) can be trained to classify sleep state. Various architectures for LSTM models exist, with many involving stacked models. For example, one LSTM model architecture that could be used is a multilayer perception structure that feeds into a recurrent neural network structure. The multilayer perception model may include a specific number of fully connected layers that will extract the hierarchical structure of the data with interspersed dropout layers to discourage the overfitting of the model to the dataset. The recurrent neural network model is used to capture the temporal information of the data, which is used for sleep state detection. LSTM networks are able to understand longer-term dependencies that are present in the data by parsing through the data in larger sequences instead of individual samples. LSTMs also have the ability to selectively remember and forget information, making them useful for this kind of application where sequences have an intrinsic cycle, such as sleep states.

The training samples for the sleep state detection model 662 may include a combination of raw capacitive grid pressure data, signals extracted from the pressure data and other supporting sensors within the intelligent surface, and sleep state labels from a clinical-grade sleep monitoring system such as those used in clinical sleep labs or those sold as clinical-level consumer systems. All data and labels are collected simultaneously and timestamped. Raw pressure data is provided from the capacitive sensing layer as a time-series of matrices, where each matrix represents the pressure detected by the grid of capacitive pressure sending points that may be in unitless, raw integer form. In some embodiment, this data is not calibrated. The data is used by the weight support system 110 in its original integer state and not as a processed float of real pressure units (i.e. mmHg, PSI, etc.).

Example training samples look something like the following, arranged in a table with further processed features. Other data in training samples may also include movement, the respiration and heart rate.

| ID | Sleep state | Body position | Joint1 x, y | Joint2 x, y | Joint3 x, y |
|---|---|---|---|---|---|
| 0 | N1 | Back | 12.24 | 30.18 | 45.5 |
| 1 | N1 | Back | 12.24 | 30.17 | 46.5 |

In the table above, more features continue on the right side of the table and more samples continue on the bottom of the table.

Both this time-series of frames and various other pressure-specific time-series signals (i.e. average and peak pressure over time) created from this time-series of frames may be used to train the machine learning models used for sleep state detection.

Biometrics such as respiration rate and heart rate may also be part of the inputs for sleep state detection. These signals, in their raw form (i.e. thoracic effort) can be extracted from the capacitive pressure frames using signal processing, supplemented by signals from supporting sensors. These can be further processed by feeding them into FIR filters to extract the respiration and heart rate in BPM.

The output sleep state labels may be provided by the clinical-grade sleep monitoring system as text labels for every 30-second segment. Segments can be labeled as awake, N1, N2, N3, or REM sleep. A person's sleep architecture typically consists of several different phases (referred to as sleep states) which repeat during the night. These states are distinguished as REM (rapid eye movement) and NREM (non-rapid eye movement) sleep. The commonly used sleep states are the NREM states of N1, N2, N3, and the REM state. These states can be identified by different physiological changes and certain states (particularly the N3 and REM) are critical for tissue recovery and energy restoration. Maintaining an appropriate amount of time in these important sleep stages has been shown to promote good health.

Automatic Turn Detection and Graphical User Interface

Figure 7A:
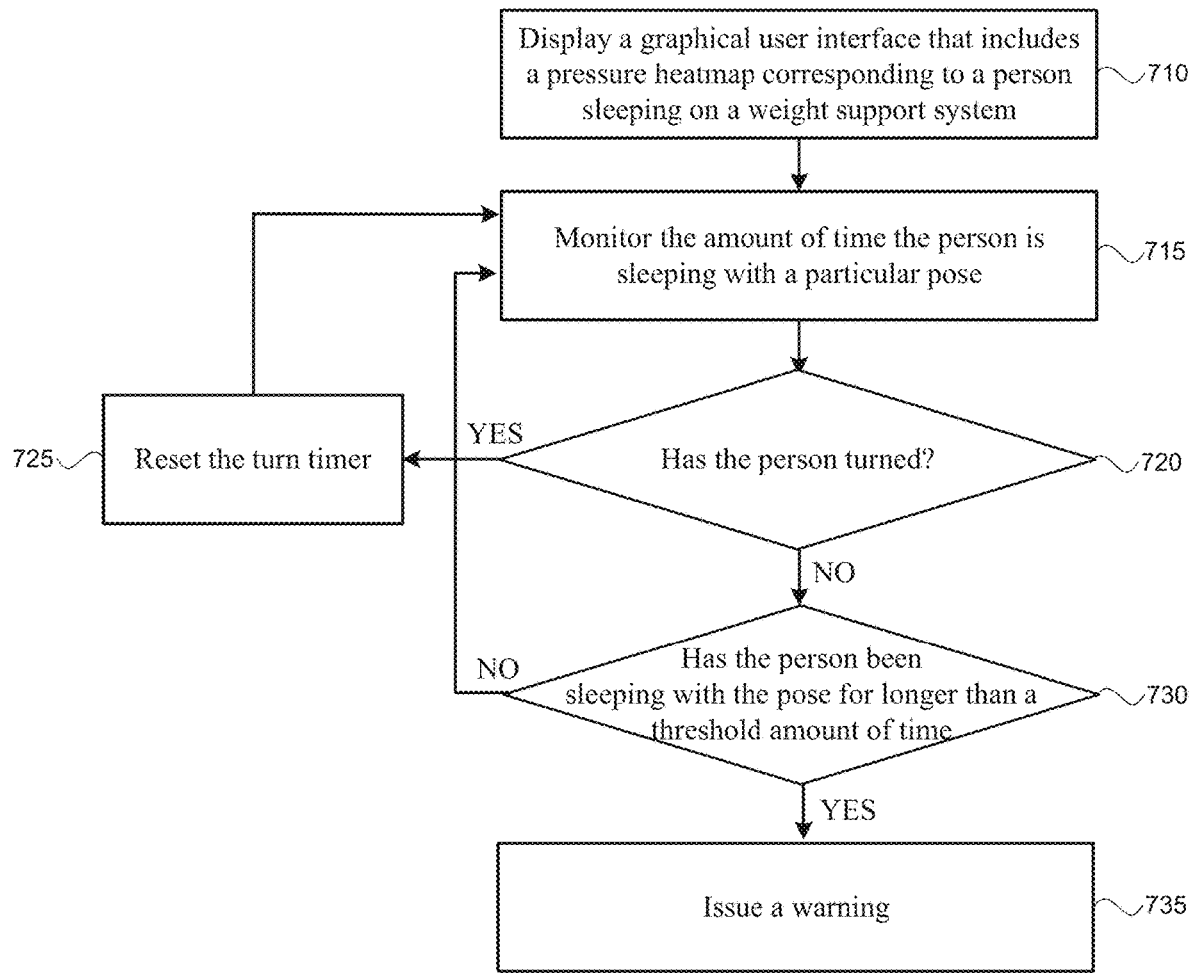
FIG. 7A is a flowchart depicting an example of process for monitor sleep of a person using a weight support system, in accordance with some embodiments.
Figure 7B:
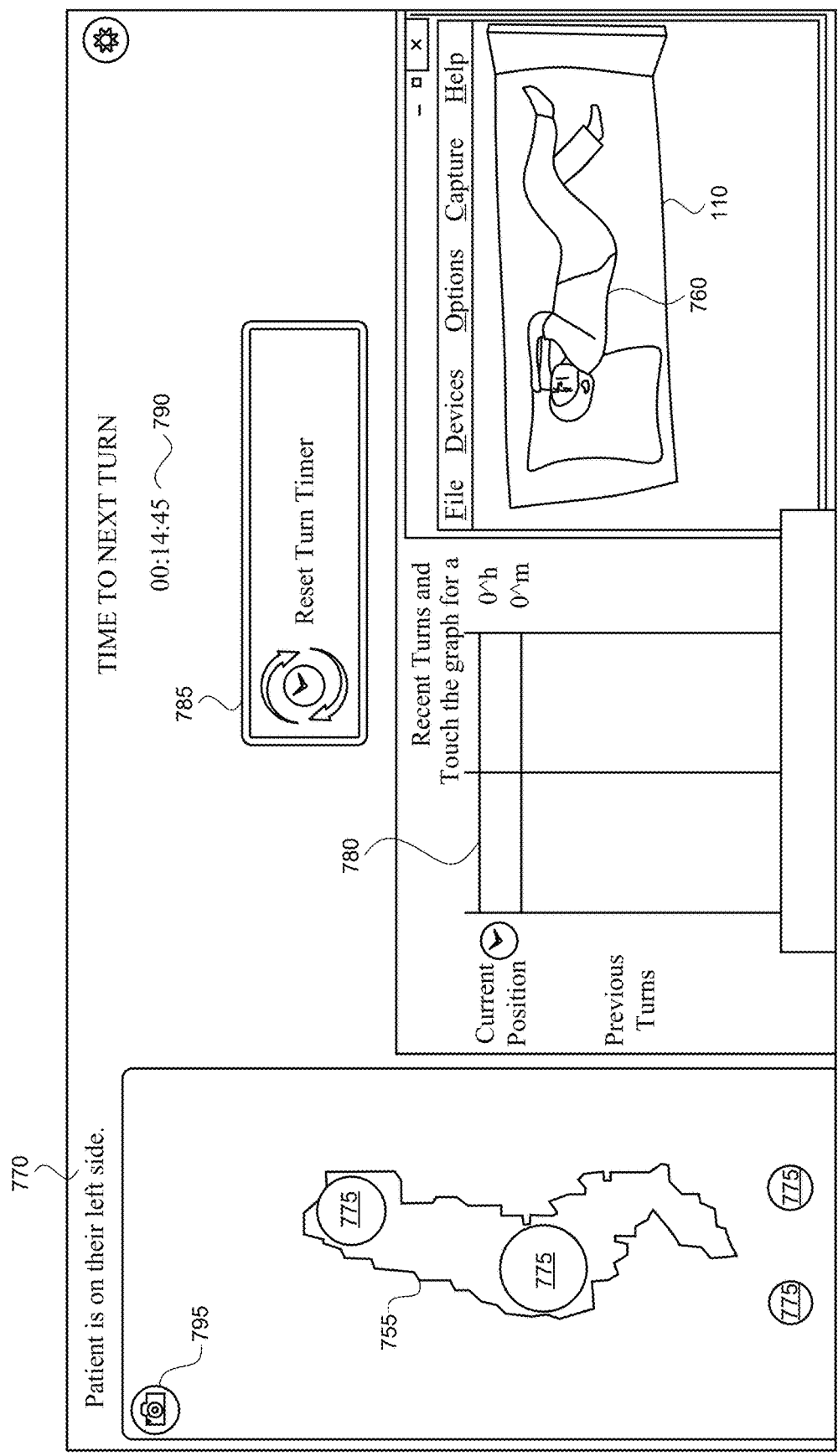
FIG. 7B is a conceptual diagram illustrating an example graphical user interface, in accordance with some embodiments.

FIG. 7A is a flowchart depicting an example process 700 for detecting turns and other change of poses of a sleeping person, in accordance with some embodiments. FIG. 7B is a conceptual diagram illustrating an example graphical user interface that monitors the sleep status of a person, in accordance with some embodiments. FIG. 7A is discussed in conjunction with FIG. 7B.

In some embodiments, a computer displays 710 a graphical user interface (GUI) 750 that includes a pressure heatmap 755 corresponding to a person 760 sleeping on a weight support system 110. The GUI 750 may be an example of the interface 175 shown in FIG. 1. At a particular instance in time, the GUI 750 may display information related to the pose of the person 760, such as the side label 770. The GUI 750 may also display one or more symbols that are used to represent key body parts, such as key joints locations, detected by the computer. For example, in the example GUI 750, the symbols are circles 775 of different sizes that represent the locations of various key body parts of the person 760. The GUI 750 may also include a time progress tracker 780 that tracks the poses and positions of the person 760 over time. The time progress tracker 780 may display the turns and the poses of the person 760 as a timeline. The time progress track 780 may also be interactive. For example, a user (e.g., the person 760 or a clinician) may rewind to a particular time instance and the heatmap 755 will show the pressure distribution of the person 760 at the particular time instance. The user may also capture the heatmap 755 using button 795.

The identification of the poses, joint locations, and side labels are discussed above with reference to FIG. 6A through FIG. 6D. U.S. Pat. No. 9,320,665, entitled "Risk Modeling for Pressure Ulcer Formation," patented on Apr. 26, 2016, is also incorporated by reference herein for all purposes.

The circles 775 may display different colors that represent the level of pressure, time, or time lapse for a particular body part that has experienced a particular level of pressure. For example, the GUI 750 may provide various settings for a user to specify the threshold value for a circle to change 775 to change color. For example, a circle 775 may be in a first color (e.g., yellow) for a certain level of pressure and may turn to a second color (e.g., red) if the level of pressure detected at the body part exceeds the threshold level of pressure. In some embodiments, the change of color may also be used to indicate other conditions, such as the particular body part has been under pressure for a prolonged period of time.

The computer monitors 715 the amount of time the person 760 is sleeping with a particular pose, such as on a particular side. The GUI 750 may display a timer 790 to keep track of the amount of time associated with the pose. The timer 790 may take the form of time progress or time lapse. For example, a user, in the setting, may specify the maximum amount of time the person 760 should sleep with a particular pose before the person 760 should turn. The time may also be automatically determined by the computing system or be a predetermined amount.

In the decision stage 720, the computer determines whether the person 760 has turned. If the person 760 has turned, the computer automatically resets 725 the turn timer and record the turning time in the system memory. The button 785 may also be used to reset the turn timer manually such as by a clinician. If the person 760 has not turned, the computer determines 730 whether the person 760 has been sleeping with the pose for longer than a threshold amount of time. If so, the computer may issue 735 a warning, such as sending to warning to a clinician to have the clinician to help the person 760 to turn. If the person 760 has been sleeping with the poser for shorter than the threshold, the computer continues to monitor 715 the amount of time the person is sleeping with the pose. Throughout the process, the computer may also determine the sleep state of the person 760. The computer may continue to keep track of the sleep status of the person 760 throughout the night and generate a report in the morning that can be reviewed in a software application.

Additional Example Uses of the Weight Support System

Additionally or alternatively, the detection of body movement, respiration and heart rates, and body, joint, and limb positions generated from the data analysis can be used on their own outside of sleep state detection to provide more information to clinicians.

Activity level can be derived from a number of different signals extracted from the intelligent surface. Average pressure over time can be used to identify when a body is moving on top of the intelligent surface. The change in body, joint, and limb position can be used to more granularly identify when a specific part of the user's body has moved. By combining those two together, activity level and the movement of a body segment can be used to inform clinical decisions.

Seizures, formally known as epileptic seizures, are a period of symptoms due to abnormal neuronal activity in the brain. Seizures that last for more than a brief period are considered a medical emergency and those lasting longer than 5 minutes are called status epilepticus (SE) and are a life-threatening medical emergency. The intelligent surface could be used to provide an alert and actionable information to clinical staff if a patient on top of the surface experiences a seizure. While signs and symptoms of seizures will vary with the type, the majority of seizures are known as convulsive, beginning as either a focal seizure and becoming generalized or starting and staying a generalized seizure. For focal seizures, symptoms may include jerking activity starting in a specific muscle group and moving to surrounding muscle groups such as the smacking of lips or unconscious jerking to pick up and object. For generalized seizures, symptoms will include the sudden loss of consciousness and may include uncontrolled contraction and extension of the limbs, the prolonged arching of the back for 10-30 seconds, convulsion of limbs in unison, muscles spasms in a few limbs or the entire body. Because the intelligent surface can be used to detect movement of the body as well as the movement of specific limbs or joints over time, these features can be fed into a system of machine learning models to detect seizure occurrence. For example, if when tracking the movement of the patient, all limbs convulse in unison, the time at which that set of movements started can be recorded and a notification sent to clinical staff to check on the patient. If they are experiencing a seizure, the start time can be used by the clinician to determine if the event is an SE or a regular seizure in order to better provide treatment, given the knowledge that SEs are considered medical emergencies and can be life threatening with delayed treatment.

Surface or bed occupancy can be useful clinical information for a variety of applications, including monitoring in long term care homes where patients are encouraged to adhere to an activity schedule and avoid roaming at certain times of the day. While a basic threshold can be used to determine occupancy based on a general average pressure value, more intelligent occupancy detection systems can be used by leveraging the intelligent surface's body, joint, and limb position systems.

Fall detection provides an important service in spaces where high-risk populations like seniors are treated. Because seniors and other high-risk populations are more prone to injury and extended periods of healing after a fall, detecting when a patient is about to fall off the bed and preventing that is important in reducing length of stay and amount of injury for those patients. With the capacitive pressure sensor grid fully mapping the surface that the patient is lying on, multiple features such as if the patient is on the edge of the bed, their body position, the speed at which their joints and limbs are moving across the intelligent surface, can all be used together in a fall detection system. This system may be simply an algorithm that takes in these features or it may involve machine learning models that are trained on fall datasets to detect when a patient on the intelligent surface is at risk of falling.

Respiratory and heart failure are major causes of death and can be caused by a variety of symptoms. If clinicians are able to catch patients at the onset or during a respiratory or a heart failure event, the patient's chances of survival are dramatically increased. Because the intelligent surface can monitor vital signs such as respiration and heart rate over time, if those detected breaths or beats per minute fall outside of healthy range and either reach extremely high or extremely low values, clinicians can be notified and provide treatment as needed depending on the type of failure and underlying causes.

Speaking, coughing, eating, and drinking are common events in both regular life and within the hospital. With certain treatments, compliance to eating or drinking may be important pieces of clinical information. For certain illnesses, the frequency and magnitude of coughing are important for clinicians. All of these events are respiration related in that they involve the pharynx and esophagus, parts of the respiratory system. In either aforementioned case, because the intelligent surface is able to extract a patient's thoracic effort when they are on the surface, this signal can be processed to understand whether the user is speaking, coughing, eating, or drinking based on the signal's characteristics. The novel invention described in this document is an "intelligent surface" that automatically detects sleep states.

The weight support system 110 may also measure shear. Shear is another indicator for skin tissue issues. This can be modeled by rapid changes in the surface pressure gradient, or also by embedding tilt or IMU sensors into the surface to measure surface contours. Rapid changes in surface contour is often an indicator of increased shear forces.

Example Architecture of Machine Learning Models

In various embodiments, a wide variety of machine learning techniques may be used for detection of a person's pose such as side labels and joint positions, identification of the person's outline, detection of the person's sleep state, identification of potential seizure, identification of imminent fall, and other uses described herein. The machine learning techniques include different forms of supervised learning, unsupervised learning, and semi-supervised learning such as decision trees, support vector machines (SVMs), regression, Bayesian networks, and genetic algorithms. Deep learning techniques such as neural networks, including convolutional neural networks (CNN) and recurrent neural networks (RNN) (e.g., long short-term memory networks (LSTM)), may also be used. For example, for the detection of the person's pose that is shown in FIG. 6C, various pattern recognition may rely on a CNN. For sleep state detection 662, an LSTM may be used.

In various embodiments, the training techniques for a machine learning model may be supervised, semi-supervised, or unsupervised. In supervised learning, the machine learning models may be trained with a set of training samples that are labeled. For example, for a machine learning model trained to classify body parts, the training samples may be different heatmap of pressure data labeled with the body parts. The labels for each training sample may be binary or multi-class. In training a machine learning model for sleep state detection, the training samples may be data of individuals in various sleep states (each sleep state may be a label). For training a binary machine learning model (e.g., a model that identifies whether a person is having a seizure, whether a person is having a condition, etc.), training samples may include a positive training set (with training samples that have the label of having the condition) and a negative training set (with training samples that have the label of not having the condition). In some cases, an unsupervised learning technique may be used. The samples used in training are not labeled. Various unsupervised learning technique such as clustering may be used. In some cases, the training may be semi-supervised with the training set having a mix of labeled samples and unlabeled samples.

A machine learning model may be associated with an objective function, which generates a metric value that describes the objective goal of the training process. For example, the training may intend to reduce the error rate of the model in generating predictions. In such a case, the objective function may monitor the error rate of the machine learning model. In object recognition (e.g., object detection and classification), the objective function of the machine learning algorithm may be the training error rate in classifying objects in a training set. Such an objective function may be called a loss function. Other forms of objective functions may also be used, particularly for unsupervised learning models whose error rates are not easily determined due to the lack of labels. In sleep state detection, the objective function may correspond to the difference between the model's prediction of the sleep state and the manually identified sleep state in the training sets. In various embodiments, the error rate may be measured as cross-entropy loss, L1 loss (e.g., the sum of absolute differences between the predicted values and the actual value), L2 loss (e.g., the sum of squared distances).

Figure 8:
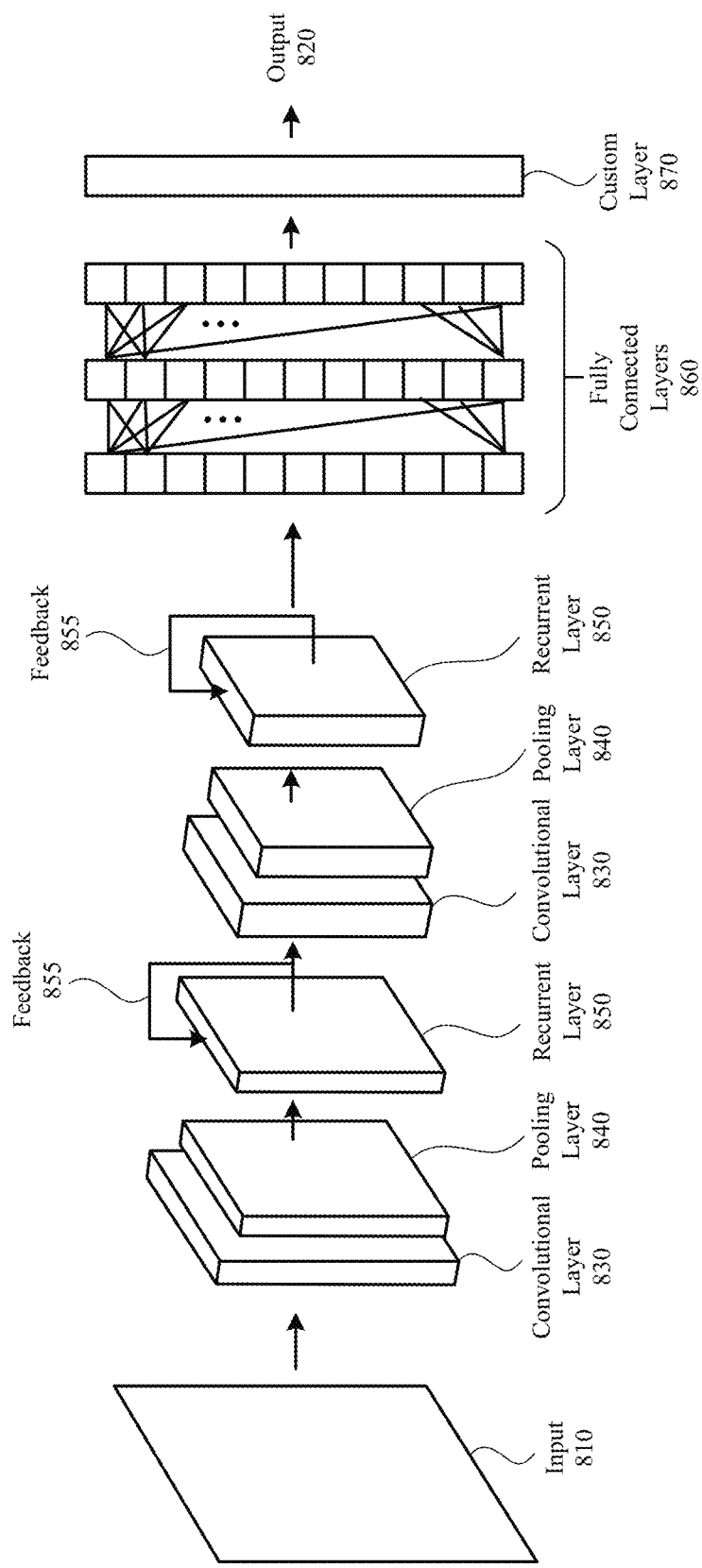
FIG. 8 is a block diagram illustrating the architecture of example machine learning models, according to some embodiments.

FIG. 8 shows an example structure of a neural network, which may include layers that may present in various machine learning models. For example, a CNN may include the convolutional layers and the pooling layers shown in FIG. 8. An LSTM may include the recurrent layers shown in FIG. 8. Each machine learning models may have its own structure and layers (while omitting some layers in FIG. 8). The order of the layers in FIG. 8 is also an example. The order of layers may change, depending on the type of machine learning model used.

Referring to FIG. 8, a structure of an example neural network (NN) is illustrated, according to an embodiment. The NN 800 may receive an input 810 and generate an output 820. The NN 800 may include different kinds of layers, such as convolutional layers 830, pooling layers 840, recurrent layers 850, full connected layers 860, and custom layers 870. A convolutional layer 830 convolves the input of the layer (e.g., an image) with one or more kernels to generate different types of images that are filtered by the kernels to generate feature maps. Each convolution result may be associated with an activation function. A convolutional layer 830 may be followed by a pooling layer 840 that selects the maximum value (max pooling) or average value (average pooling) from the portion of the input covered by the kernel size. The pooling layer 840 reduces the spatial size of the extracted features. In some embodiments, a pair of convolutional layer 830 and pooling layer 840 may be followed by a recurrent layer 850 that includes one or more feedback loop 855. The feedback 855 may be used to account for spatial relationships of the features in an image or temporal relationships of the objects in the image. The layers 830, 840, and 850 may be followed in multiple fully connected layers 860 that have nodes (represented by squares in FIG. 8) connected to each other. The fully connected layers 860 may be used for classification and object detection. In one embodiment, one or more custom layers 870 may also be presented for the generation of a specific format of output 820. For example, a custom layer may be used for image segmentation for labeling pixels of an image input with different segment labels.

The order of layers and the number of layers of the NN 800 in FIG. 8 is for example only. In various embodiments, a NN 800 includes one or more convolutional layer 830 but may or may not include any pooling layer 840 or recurrent layer 850. If a pooling layer 840 is present, not all convolutional layers 830 are always followed by a pooling layer 840. A recurrent layer may also be positioned differently at other locations of the CNN. For each convolutional layer 830, the sizes of kernels (e.g., 3×3, 5×5, 7×7, etc.) and the numbers of kernels allowed to be learned may be different from other convolutional layers 830.

A machine learning model may include certain layers, nodes, kernels and/or coefficients. Training of a neural network, such as the NN 800, may include forward propagation and backpropagation. Each layer in a neural network may include one or more nodes, which may be fully or partially connected to other nodes in adjacent layers. In forward propagation, the neural network performs the computation in the forward direction based on outputs of a preceding layer. The operation of a node may be defined by one or more functions. The functions that define the operation of a node may include various computation operations such as convolution of data with one or more kernels, pooling, recurrent loop in RNN, various gates in LSTM, etc. The functions may also include an activation function that adjusts the weight of the output of the node. Nodes in different layers may be associated with different functions.

Each of the functions in the neural network may be associated with different coefficients (e.g. weights and kernel coefficients) that are adjustable during training. In addition, some of the nodes in a neural network may also be associated with an activation function that decides the weight of the output of the node in forward propagation. Common activation functions may include step functions, linear functions, sigmoid functions, hyperbolic tangent functions (tan h), and rectified linear unit functions (ReLU). After an input is provided into the neural network and passes through a neural network in the forward direction, the results may be compared to the training labels or other values in the training set to determine the neural network's performance. The process of prediction may be repeated for other images in the training sets to compute the value of the objective function in a particular training round. In turn, the neural network performs backpropagation by using gradient descent such as stochastic gradient descent (SGD) to adjust the coefficients in various functions to improve the value of the objective function.

Multiple rounds of forward propagation and backpropagation may be performed. Training may be completed when the objective function has become sufficiently stable (e.g., the machine learning model has converged) or after a predetermined number of rounds for a particular set of training samples. The trained machine learning model can be used for performing sleep state detection, body part detection, joint identifications, or another suitable task for which the model is trained.

Computing Machine Architecture

Figure 9:
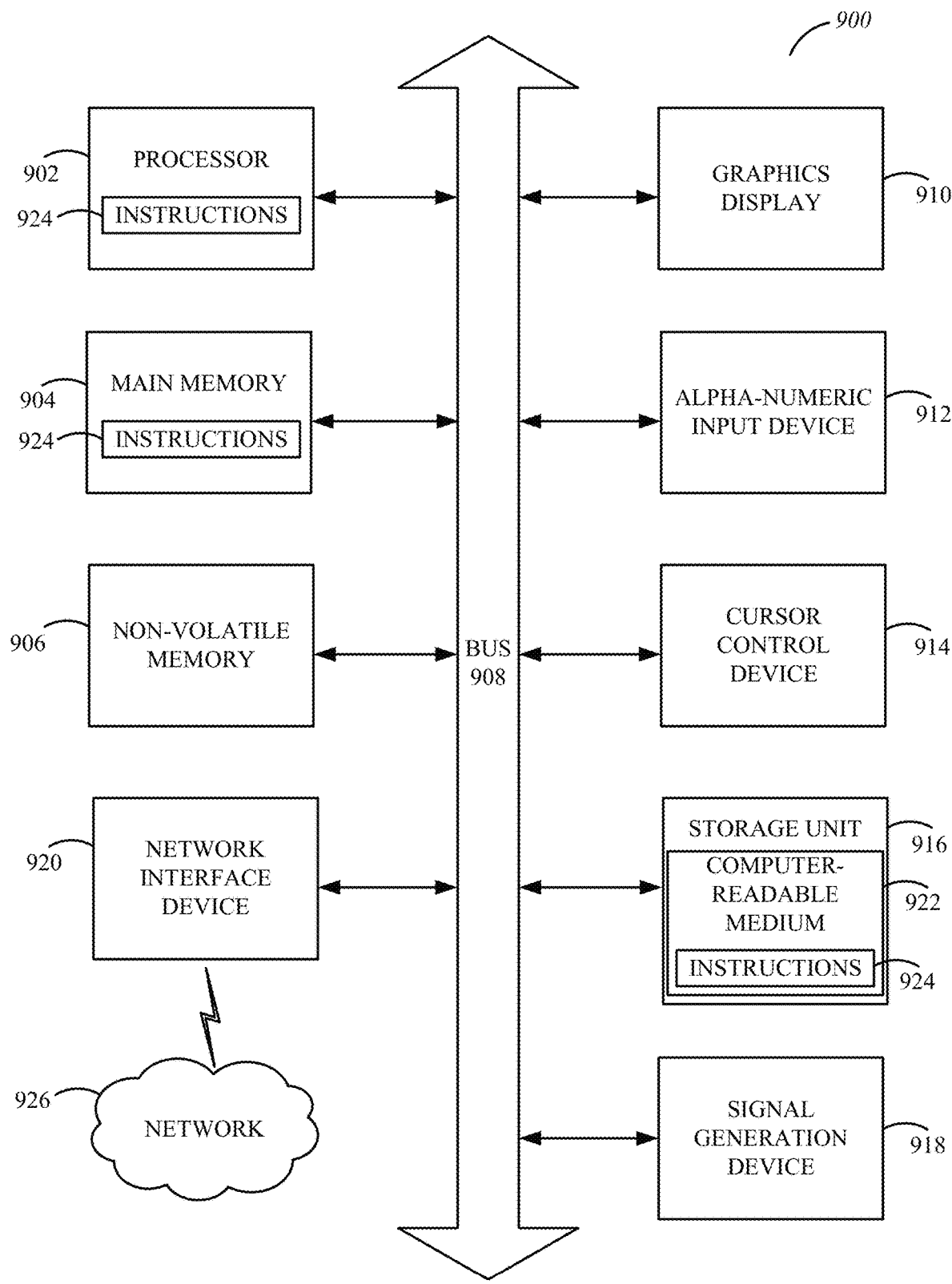
FIG. 9 is a block diagram illustrating components of example computing machines, according to some embodiments.

FIG. 9 is a block diagram illustrating components of an example computing machine that is capable of reading instructions from a computer-readable medium and execute them in a processor (or controller). A computer described herein may include a single computing machine shown in FIG. 9, a virtual machine, a distributed computing system that includes multiples nodes of computing machines shown in FIG. 9, or any other suitable arrangement of computing devices.

By way of example, FIG. 9 shows a diagrammatic representation of a computing machine in the example form of a computer system 900 within which instructions 924 (e.g., software, program code, or machine code), which may be stored in a computer-readable medium for causing the machine to perform any one or more of the processes discussed herein may be executed. In some embodiments, the computing machine operates as a standalone device or may be connected (e.g., networked) to other machines. In a network deployment, the machine may operate in the capacity of a server machine or a client machine in a server-client network environment, or as a peer machine in a peer-to-peer (or distributed) network environment.

The structure of a computing machine described in FIG. 9 may correspond to any software, hardware, or combined components shown in FIG. 1, including but not limited to, the computing server 140, the local computer 130, the data store 160, the user device 170, and any computer that performs processes such as processes 500 and 600.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 924 that specify actions to be taken by that machine. Further, while only a single machine is illustrated, the term "machine" shall also be taken to include any collection of machines that individually or jointly execute instructions 924 to perform any one or more of the methodologies discussed herein.

The example computer system 900 includes one or more processors (generally, processor 902) (e.g., a central processing unit (CPU), a graphics processing unit (GPU), a digital signal processor (DSP), one or more application-specific integrated circuits (ASICs), one or more radio-frequency integrated circuits (RFICs), or any combination of these), a main memory 904, and a non-volatile memory 906, which are configured to communicate with each other via a bus 908. The computer system 900 may further include graphics display unit 910 (e.g., a plasma display panel (PDP), a liquid crystal display (LCD), a projector, or a cathode ray tube (CRT)). The computer system 900 may also include alphanumeric input device 912 (e.g., a keyboard), a cursor control device 914 (e.g., a mouse, a trackball, a joystick, a motion sensor, or other pointing instrument), a storage unit 916, a signal generation device 918 (e.g., a speaker), and a network interface device 920, which also are configured to communicate via the bus 908.

The storage unit 916 includes a computer-readable medium 922 on which is stored instructions 924 embodying any one or more of the methodologies or functions described herein. The instructions 924 may also reside, completely or at least partially, within the main memory 904 or within the processor 902 (e.g., within a processor's cache memory) during execution thereof by the computer system 900, the main memory 904 and the processor 902 also constituting computer-readable media. The instructions 924 may be transmitted or received over a network 926 via the network interface device 920.

While computer-readable medium 922 is shown in an example embodiment to be a single medium, the term "computer-readable medium" should be taken to include a single medium or multiple media (e.g., a centralized or distributed database, or associated caches and servers) able to store instructions (e.g., instructions 924). The computer-readable medium may include any medium that is capable of storing instructions (e.g., instructions 924) for execution by the machine and that cause the machine to perform any one or more of the methodologies disclosed herein. The computer-readable medium may include, but not be limited to, data repositories in the form of solid-state memories, optical media, and magnetic media. The computer-readable medium does not include a transitory medium such as a signal or a carrier wave.

Example Circuitry for Weight Support System

Figure 10:
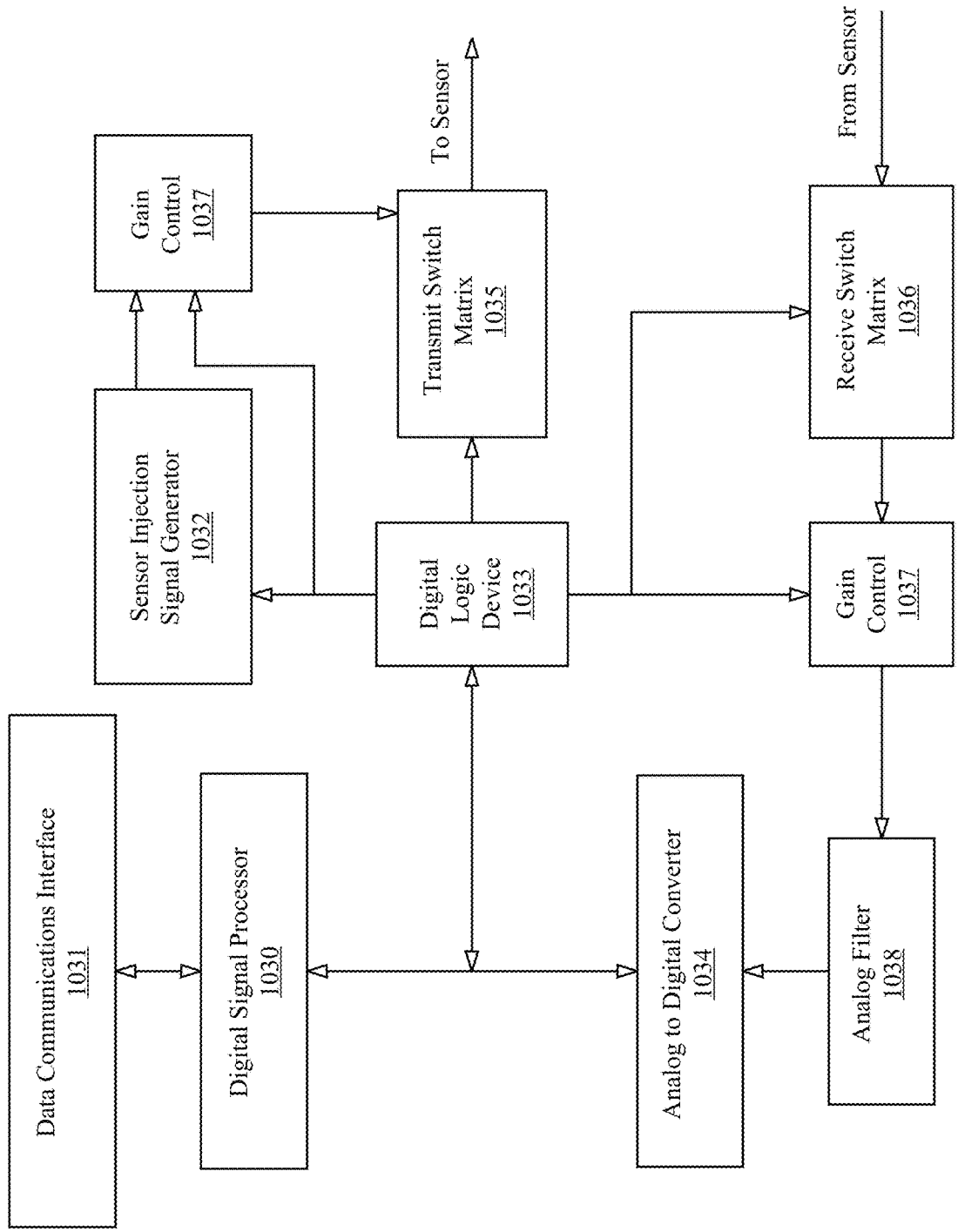
FIG. 10 is a block diagram illustrating example circuitry of a weight support system, in accordance with some embodiments.

FIG. 10 is a block diagram illustrating an example circuitry of a weight support system 110, in accordance with some embodiments. The circuitry of a weight support system 110 may include a digital signal processor (DSP) 1030, injection signal generation and control 1032, 1037, 1035, signal detection and control 1036, 1037, 1038, 1034, a digital logic device 1033, and a data communications interface 1031.

The DSP 1030 executes firmware that is designed to receive control messages from application software running on a personal computer or embedded computer via the data communications interface 1031. The control messages may include measurement requests that contain coordinates for an individual sensing element (sensel) within the pressure sensor array. The DSP 1030 selects a column for the injection signal and a row for signal detection. The detected signal is then converted from analog to digital 1034 for measurement processing by the DSP 1030. The measurement is then passed back to the application software via the data communications interface 1031.

The DSP 1030 may be a standalone device or include external memory such as Random Access Memory (RAM), Read Only Memory (ROM), or any other commonly used memory device. Memory devices can be accessed either serially or via parallel data bus.

The sensor injection signal generation block 1032 is an electronic device or circuit used to create a sinusoidal injection signal at a selectable frequency. The injection signal can be in the range of 1 kHz to 5 MHz, or preferably 1 kHz to 250 kHz.

The gain control block 1037 is an electronic device or circuit used to adjust the amplitude of the injection signal. The gain setting is controlled by the DSP 1030 via the digital logic device 1033. The amplified injection signal is connected to the transmit switch matrix 1035. The DSP 1030 configures the digital logic device 1033 to enable the appropriate switch in the switch matrix in order to select a sensor column for transmitting the injection signal.

The injection signal passes through the pressure sensor and is detected on a row selected using the receive switch matrix 1036. The sensor row is selected by the DSP 1030 via the digital logic device 1033 and the selected signal is connected to the gain control block 1037 for amplification.

An analog filter 1038 removes signal noise before the analog to digital converter (ADC) 1034. The analog filter is an electronic device or circuit that acts as a band pass or low pass filter and only passes frequencies near the injection signal frequency. For example, if the injection signal has a frequency of 250 kHz the filter only passes frequencies in the range of 200 kHz to 350 kHz and thereby rejects other interfering signals that are not within the pass band. The analog filter can be designed to accommodate pass bands of variable frequency spreads where tighter frequency spreads more effectively filter interfering signals.

The ADC 1034 is periodically sampled by the DSP 1030 in order to acquire sufficient samples for performing a measurement calculation. For example, 12, 24, 48, 96, or 192 samples can be acquired before performing a measurement calculation on the samples. The DSP 1030 can also execute firmware to perform additional digital filtering in order to further reduce the frequency spread of the pass band and more effectively filter interfering signals. Digital filtering requires more samples from the ADC 1034, for example in the range of 50 to 2500 samples, or preferably 512 samples.

The data communications interface 1031 passes data between the DSP 1030 and the application software running on the Control Processor Unit. The interface includes electronic devices or circuitry to perform wired or wireless communication. Examples of wired communication include RS232 serial, Universal Serial Bus (USB), Ethernet, fibreoptic, or any other serial or parallel data communication technology. Examples of wireless communication include, Zigbee, Bluetooth, WiFi, Wireless USB, or any other wireless data communication technology.

The digital logic device 1033 includes electronic devices or circuitry, for example complex programmable logic devices (CPLD), field programmable gate arrays (FPGA), application specific integrated circuits (ASIC), or discrete logic devices. Alternatively, the DSP 1030 has General Purpose Input Output (GPIO) pins that may be used in place of the digital logic device to control selectable electronic devices.

ADDITIONAL CONSIDERATIONS

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Embodiments according to the invention are in particular disclosed in the attached claims directed to a method and a computer program product, wherein any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter which can be claimed comprises not only the combinations of features as set out in the disclosed embodiments but also any other combination of features from different embodiments. Various features mentioned in the different embodiments can be combined with explicit mentioning of such combination or arrangement in an example embodiment. Furthermore, any of the embodiments and features described or depicted herein can be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

What is claimed is:

1. An air-permeable bedding system, comprising:
   an inlet configured to be connected to an active air source;
   a microclimate fabric layer; and
   an air-permeable capacitive sensor layer below the microclimate fabric layer, the air-permeable capacitive sensor layer comprising a top air-permeable substrate, a bottom air-permeable substrate, and an air-permeable dielectric layer, wherein:
   the top and bottom air-permeable substrates are separated vertically by the air-permeable dielectric layer that is located between the top and bottom air-permeable substrates,
   the air-permeable dielectric layer is configured to receive air flow horizontally from the active air source,
   the air-permeable dielectric layer comprises a plurality of cut-outs,
   the top air-permeable substrate is laminated with a top set of electrically conductive pathways,
   the bottom air-permeable substrate is laminated with a bottom set of electrically conductive pathways,
   the electrically conductive pathways of the top set of electrically conductive pathways are parallel to each other and the electrically conductive pathways of the bottom set of electrically conductive pathways are parallel to each other and the top set of electrically conductive pathways and the bottom set of electrically conductive pathways are rotated at an angle relative to each other to form a grid,
   the parallel electrically conductive pathways in the top set are spaced apart from each other to form a top set of horizontal air pathways,
   the parallel electrically conductive pathways in the bottom set are spaced apart from each other to form a bottom set of horizontal air pathways,
   the top set of electrically conductive pathways and the bottom set of electrically conductive pathways are separated vertically by the air-permeable dielectric layer that is configured to receive air flow horizontally from the active air source
   the top set and the bottom set of horizontal air pathways intersect with each other and intersect with the plurality of cut-outs of the air-permeable dielectric layer to form vertical air pathways such that airflow passes vertically through a plurality of gaps of the grid and horizontally through the air-permeable dielectric layer, and
   one of the top set of electrically conductive pathways and the bottom set of electrically conductive pathways is configured to transmit electrical signals to another one of the top set of electrically conductive pathways and the bottom set of electrically conductive pathways and the another one of the top set of electrically conductive pathways and the bottom set of electrically conductive pathways is configured to receive the electrical signals.

2. The air-permeable bedding system of claim 1, wherein the top air-permeable substrate and the bottom air-permeable substrate are formed from meshes or foam.

3. The air-permeable bedding system of claim 1, wherein at least one electrically conductive pathways of the top set of electrically conductive pathways and the bottom set of electrically conductive pathways is encapsulated by a thermoplastic.

4. The air-permeable bedding system of claim 3, wherein the thermoplastic is bonded to the one of the top air-permeable substrate and the bottom air-permeable substrate.

5. The air-permeable bedding system of claim 4, wherein the thermoplastic is bonded to the one of the top air-permeable substrate and the bottom air-permeable substrate by heat lamination.

6. The air-permeable bedding system of claim 1, further comprising:
   a foam comfort layer between the microclimate fabric layer and the air-permeable capacitive sensor layer.

7. The air-permeable bedding system of claim 1, further comprising:
   a piezoelectric sensor below the microclimate fabric layer.

8. The air-permeable bedding system of claim 7, further comprising a transmitter configured to transmit signals of the capacitive sensor layer for determining a respiration rate and to transmit signals of the piezoelectric sensor for determining a heart rate.

9. The air-permeable bedding system of claim 1, further comprising:
   an inlet configured to be connected to an active air source that increases airflow within the air-permeable bedding system.

\* \* \* \* \*